(12) United States Patent
Sekimizu et al.

(10) Patent No.: US 8,313,779 B2
(45) Date of Patent: Nov. 20, 2012

(54) EVALUATION METHOD AND SCREENING METHOD FOR SUBSTANCE HAVING ACTION OF ACTIVATING/SUPPRESSING INNATE IMMUNITY, AGENT AND FOOD PRODUCT FOR ACTIVATING/SUPPRESSING INNATE IMMUNE MECHANISM AND METHOD FOR PRODUCING THE SAME

(75) Inventors: Kazuhisa Sekimizu, Tokyo (JP); Hiroshi Hamamoto, Tokyo (JP)

(73) Assignees: Genome Pharmaceuticals Institute Co., Ltd., Tokyo (JP); The University of Tokyo, Tokyo (JP); Imagine Global Care Corporation, Tokyo (JP)

( * ) Notice: Subject to any disclaimer, the term of this patent is extended or adjusted under 35 U.S.C. 154(b) by 415 days.

(21) Appl. No.: 12/595,245

(22) PCT Filed: Apr. 10, 2008

(86) PCT No.: PCT/JP2008/057105
§ 371 (c)(1),
(2), (4) Date: Oct. 9, 2009

(87) PCT Pub. No.: WO2008/126905
PCT Pub. Date: Oct. 23, 2008

(65) Prior Publication Data
US 2010/0111870 A1 May 6, 2010

(30) Foreign Application Priority Data
Apr. 10, 2007 (JP) .................................. 2007-102918

(51) Int. Cl.
*A61K 35/12* (2006.01)
*A61K 35/34* (2006.01)
*A61K 49/00* (2006.01)
*C12Q 1/02* (2006.01)

(52) U.S. Cl. ......... 424/548; 424/572; 424/520; 424/9.1; 435/29

(58) Field of Classification Search .................... None
See application file for complete search history.

(56) References Cited

FOREIGN PATENT DOCUMENTS
WO 01 86287 11/2001

OTHER PUBLICATIONS

Website document entitled: "MedlinePlus: Allergy Testing". Available at http://www.nlm.nih.gov/medlineplus/ency/article/003519.htm. (downloaded from website Jan. 5, 2012).*
Sekimizu et al. (2005) J. Biochem. 137, 199-203.*
Boldyrev et al. (2005) J. Neurochemistry 95, 913-918.*
Beutler (2004) Molecular Immunology 40, 845-859.*
Wago, H., et al., "Possibility of Utilization of Immunostimulatory Substances for Fish Culture", " Mixed Feed B", vol. 35, No. 1, pp. 118-119 (1998) (with English translation).
Wang, Y. et al., "Biological activity of Manduca sexta paralytic and plasmatocyte spreading peptide and primary structure of its hemolymph precursor", Insect Biochemistry and Molecular Biology, vol. 29, No. 12, pp. 1075-1086 (1999).
Maggi, C. A., et al., "Direct evidence for the involvement of vasoactive intestinal polypeptide in the motor response of the human isolated ileum to capsaicin", European Journal of Pharmacology, vol. 185, No. 2/3, pp. 169-178 (Aug. 28, 1990).
Ortego, F. et al., "Characterization and Distribution of Digestive Proteases of the Stalk Corn Borer, *Sesamia nonagrioides* Lef.", (*Lepidoptera: Noctuidae*), Archives of Insect Biochemistry and Physiology, vol. 33, No. 2, pp. 163-180 (1996).
Ishii, K., et al., "Activation of the Silkworm Cytokine by Bacterial and Fungal Cell Wall Components via a Reactive Oxygen Species-triggered Mechanism", Journal of Biological Chemistry, vol. 283, No. 4, pp. 2185-2191 (Jan. 25, 2008).
Shizuo Akira, et al., "Pathogen Recognition and Innate Immunity", Cell, vol. 124, XP003018351, Feb. 24, 2006, pp. 783-801.
Kazuhisa Sekimizu, et al., "D-Glutamic Acid-Induced Muscle Contraction in the Silkworm, *Bombyx mori*", Journal of Biochemistry, vol. 137, No. 2, XP002587097, Feb. 2005, pp. 199-203.
M. A. Azuine, et al., "Protective Role of Aqueous Turmeric Extract Against Mutagenicity of Direct-Acting Carcinogens as well as Benzo[a]pyrene-induced Genotoxicity and Carcinogenicity", Journal of Cancer Research and Clinical Oncology, vol. 118, XP000916132, Jan. 1, 1992, pp. 447-452.

* cited by examiner

*Primary Examiner* — Chris R Tate
*Assistant Examiner* — Russell Fiebig
(74) *Attorney, Agent, or Firm* — Oblon, Spivak, McClelland, Maier & Neustadt, L.L.P.

(57) ABSTRACT

It is intended to provide an evaluation method and a screening method capable of eliminating a substance that disturbs in vivo kinetics in an individual and capable of simply and easily searching a substance having an action of activating/suppressing an innate immune mechanism without being affected by LPS derived from bacteria, which can be contaminated during the search, as well as a drug and a food for activating/suppressing the innate immune mechanism, and methods of producing the same. The present invention provides a method of evaluating or screening the substance having the action of activating/suppressing the innate immune mechanism using a muscular contraction of an organism having the innate immune mechanism as an indicator, and methods of producing the drug and the food for activating/suppressing the innate immune mechanism. Also, an innate immunity activator and the food having the action of activating the innate immune mechanism containing the substance having the action of contracting the muscle of the organism having the innate immune mechanism, and an innate immunity suppressor and the food having the action of suppressing the innate immunity containing the substance having the action of suppressing the contraction of the muscle of the organism having the innate immune mechanism are provided.

6 Claims, 12 Drawing Sheets

Fig. 7

| Source of LPS | LPS | | Air | |
|---|---|---|---|---|
| | Amount of injection (μg) | Contraction value (C) | Amount of injection (mL) | Contraction value (C) |
| Saline | 0 | 0 | 0.2 | 0.31 |
| Escherichia coli | 12.5 | 0 | 0.2 | 0.31 |
| | 1.3 | -0.04 | 0.2 | 0.25 |
| Vibrio cholera (Inaba 569B) | 12.5 | -0.01 | 0.2 | 0.29 |
| Pseudomonas aeruginosa (10(Habs)) | 12.5 | -0.03 | 0.2 | 0.29 |
| Klebsiella pneumoniae | 12.5 | 0 | 0.2 | 0.33 |
| New serum type Shigella flexneri (1A) | 12.5 | -0.01 | 0.2 | 0.28 |

Serum type in parenthesis

EVALUATION METHOD AND SCREENING METHOD FOR SUBSTANCE HAVING ACTION OF ACTIVATING/SUPPRESSING INNATE IMMUNITY, AGENT AND FOOD PRODUCT FOR ACTIVATING/SUPPRESSING INNATE IMMUNE MECHANISM AND METHOD FOR PRODUCING THE SAME

CROSS-REFERENCE TO RELATED APPLICATIONS

This application is a National Stage of PCT/JP08/057,105 filed Apr. 10, 2008 and claims the benefit of JP 2007-102918 filed Apr. 10, 2007.

TECHNICAL FIELD

The present invention relates to an evaluation method and a screening method for a substance having an action of activating/suppressing an innate immune mechanism, and a drug and a food for activating/suppressing the innate immune mechanism and a method of producing the same.

BACKGROUND ART

Higher vertebrate animals such as human beings have two types of immune mechanisms (immune system), i.e., an innate immunity and an acquired immunity, and are protected from infection by allowing both the immune mechanisms to act appropriately. Meanwhile, many remaining organisms such as insects do not have the acquired immune mechanism, and are protected from the infection by the innate immune mechanism alone.

The innate immune mechanism is a defense mechanism against infection that the organisms have in common, and is characterized by its rapid reactions and effectively working against many infectious sources because this mechanism is non-specific. In the higher vertebrate animals including the human beings, it is believed that the non-specific innate immunity is more important in terms of resistance in early infection, prevention of cancers and lifestyle related diseases and tissue repair than the acquired immunity specific for the infectious source.

The infections with many infectious sources activate antigen-presenting cells such as macrophages and dendritic cells, and induce the production of cytokines such as IL-1, IL-6, IL-12 and TNF-α in the innate immune mechanism. These cytokines act upon NK cells to induce the production of IFN-γ. This produced IFN-γ acts upon the macrophages to amplify the production of IL-12 and additionally also induces the production of NO. NO rapidly reacts with oxygen and superoxide, and various chemicals produced during its process destroy the infectious source.

The abnormality in the innate immune mechanism causes various diseases. Therefore, development of excellent innate immunity activators and innate immunity suppressors capable of desirably regulating such an innate immune mechanism has been desired. Conventionally, when a substance that can be an active ingredient of such innate immunity activators and innate immunity suppressors is searched, a method in which a material to be tested is added to cultured immunocompetent cells such as macrophages from a mammalian animal and release of the cytokine such as IL-6 and TNF-α is detected by ELISA has been employed.

However, in such a conventional method, equipments for culturing the cells are required, and there has been a problem that a substance that has problems for pharamaco-kinetics in an individual when administered to the individual is also detected. Also, lipopolysaccharide (LPS) derived from bacteria and contaminated in the material to be tested reacts at low concentration, thus many materials to be tested exhibit false positive, and this has been an obstacle in the search of a novel substance.

In recent years, the method of screening the substance that acts upon the innate immune mechanism utilizing transgenic *Drosophila* has been proposed (e.g., see Patent Document 1), but a body length is very short, and thus it is difficult to inject a certain amount of a test liquid into a body fluid or an intestine, which is possible in silkworm larvae. It is also difficult to isolate an organ to subject to a pharmacological experiment, which is also possible in the silkworm larvae. Further, in this method, there is also a problem that only a mechanism to which a particular antibacterial peptide is related can be detected because a reporter gene is introduced downstream of an antibacterial peptide gene.

Patent Document 1: JP 2004-121155-A

DISCLOSURE OF INVENTION

Problem to be Solved by the Invention

The present invention intends to solve the above problems and accomplish the following objects. That is, it is an object of the present invention to provide an evaluation method and a screening method in which a substance that has problems in pharmaco-kinetics in an individual can be excluded, no effect of lipopolysaccharide (LPS) derived from bacteria, which can be contaminated during the search is given, or a substance having an action of activating/suppressing an innate immune mechanism can be searched simply and easily. Further, it is another object of the present invention to provide a substance having the action of activating/suppressing the innate immune mechanism, obtained by the method, as well as a drug and a food for activating/suppressing the innate immune mechanism, utilizing the substance, and a method of producing the same.

Means for Solving Problem

As a result of an extensive study for solving the above problems, the present inventors obtained a finding that the innate immune mechanism was closely associated with a muscular contraction mechanism in organisms such as silkworm larvae having the innate immune mechanism. And the presence of the following mechanism was found in the association of these two mechanisms.

That is, first, an innate immunity activation substance such as peptideglycan is bound to a receptor on an immunocompetent cell (or humoral), and as a result, a reactive oxygen species (ROS) is produced. This facilitates a cascade of proteases, and leads to a change from a precursor (inactivated type) to an activated form of a (*Bombyx mori*) paralytic peptide BmPP in the silkworm larva. And the activated BmPP directly (or indirectly) acts upon a muscle cell to induce a muscular contraction.

The present inventors have found by utilizing this new finding that the substance having the action of activating/suppressing the innate immune mechanism can be screened efficiently and simply using the muscular contraction in the organism such as silkworm larva having the innate immune mechanism as an indicator. Further, the present inventors have found that the action of activating the innate immune mechanism is actually present in an extract of turmeric with hot water, and completed the present invention.

As described above, conventionally, when the substance having the action of activating/suppressing the innate immune mechanism is searched, the method in which the material to be tested is added to the cultured immunocompetent cells such as macrophages and the release of the cytokine such as IL-6 and TNF-α is detected by ELISA has been employed. However, in this method, the equipments for culturing the cells are required, and there has been the problem that the substance that has problems for pharmaco-kinetics in the individual when administered to the individual is also detected. Also, lipopolysaccharide (LPS) derived from bacteria and contaminated in the material to be tested reacts at low concentration, thus many materials to be tested exhibit a possibility of having the action of activating the innate immune mechanism (exhibit false positive), and this has been the obstacle in the search of the novel substance.

On the contrary, in the screening (search) method of the present invention using the muscular contraction of the organism such as silkworm larva having the innate immune mechanism as the indicator, no ambitious equipment is required, and it becomes possible to extremely simply search the substance having the action of activating/suppressing the innate immune mechanism. Since the material to be tested is administered to the individual such as the silkworm larva, the substance that has problems for pharmaco-kinetics in the individual can be excluded during the search. Further, since lipopolysaccharide (LPS) derived from the bacteria does not cause the muscular contraction in the organism such as silkworm larva having the innate immune mechanism (see Example described later), the problem of the false positive due to LPS contaminated in the material to be tested and derived from the bacteria can be solved, and it becomes possible to detect the innate immunity activation substance other than LPS.

The present invention is based on the above finding of the present inventors, and is as follows, as the means for solving the problems. That is, <1> A method of evaluating whether a material to be tested has an action of activating an innate immune mechanism or not, comprising
(a) a step of administering the material to be tested to an organism having the innate immune mechanism; and
(b) a step of evaluating whether the material to be tested contracts a muscle of the organism having the innate immune mechanism or not (first evaluation method).

<2> A method of screening a substance having an action of activating an innate immune mechanism, comprising
(a) a step of administering a material to be tested to an organism having the innate immune mechanism;
(b) a step of evaluating whether the material to be tested contracts a muscle of the organism having the innate immune mechanism or not; and
(c) a step of selecting a substance evaluated to contract the muscle of the organism having the innate immune mechanism (first screening method).

<3> The method according to <1> or <2>, wherein the organism having the innate immune mechanism is an organism having the innate immune mechanism alone.

<4> The method according to <3>, wherein the organism having the innate immune mechanism alone is an organism belonging to insects.

<5> The method according to <4>, wherein the organism belonging to insects is a silkworm larva.

<6> A method of producing a drug for activating an innate immune mechanism, comprising
(a) a step of administering a material to be tested to an organism having the innate immune mechanism;
(b) a step of evaluating whether the material to be tested contracts a muscle of the organism having the innate immune mechanism or not;
(c) a step of selecting a substance evaluated to contract the muscle of the organism having the innate immune mechanism;
(d) a step of generating the substance selected in the step (c); and
(e) a step of mixing the substance generated in the step (d) and a pharmaceutically acceptable carrier (first drug production method).

<7> A method of producing a food having an action of activating an innate immune mechanism, comprising
(a) a step of administering a material to be tested to an organism having the innate immune mechanism;
(b) a step of evaluating whether the material to be tested contracts a muscle of the organism having the innate immune mechanism or not;
(c) a step of selecting a substance evaluated to contract the muscle of the organism having the innate immune mechanism;
(d) a step of generating the substance selected in the step (c); and
(e) a step of mixing the substance generated in the step (d) and a food raw material (first food production method).

<8> An innate immunity activator comprising a substance having an action of contracting a muscle of an organism having an innate immune mechanism as an active ingredient.

<9> The innate immunity activator according to <8>, wherein the substance having the action of contracting the muscle of the organism having the innate immune mechanism is an extract or a purified product of a vegetable.

<10> The innate immunity activator according to <8> or <9>, wherein the substance having the action of contracting the muscle of the organism having the innate immune mechanism is the extract or the purified product of turmeric.

<11> A food having an action of activating an innate immunity, comprising a substance having an action of contracting a muscle of an organism having an innate immune mechanism.

<12> The food according to <11>, wherein the substance having the action of contracting the muscle of the organism having the innate immune mechanism is an extract or a purified product of a vegetable.

<13> The food according to <11> or <12>, wherein the substance having the action of contracting the muscle of the organism having the innate immune mechanism is the extract or the purified product of turmeric.

<14> A method of evaluating whether a material to be tested has an action of suppressing an innate immune mechanism, comprising
(a') a step of administering the material to be tested and an innate immunity activation substance to an organism having the innate immune mechanism; and
(b') a step of evaluating whether the material to be tested suppresses a contraction of a muscle of the organism having the innate immune mechanism by the innate immunity activation substance, or not (second evaluation method).

<15> A method of screening a substance having an action of suppressing an innate immune mechanism, comprising
(a') a step of administering a material to be tested and an innate immunity activation substance to an organism having the innate immune mechanism;
(b') a step of evaluating whether the material to be tested suppresses a contraction of a muscle of the organism having the innate immune mechanism by the innate immunity activation substance, or not; and (c') a step of selecting a substance evaluated to suppress the contraction of the muscle of the organism having the innate immune mechanism (second screening method).

<16> The method according to <14> or <15>, wherein the organism having the innate immune mechanism is an organism having the innate immune mechanism alone.

<17> The method according to <16>, wherein the organism having the innate immune mechanism alone is an organism belonging to insects.

<18> The method according to <17>, wherein the organism belonging to insects is a silkworm larva.

<19> A method of producing a drug for suppressing an innate immune mechanism, comprising
(a') a step of administering a material to be tested and an innate immunity activation substance to an organism having the innate immune mechanism;
(b') a step of evaluating whether the material to be tested suppresses a contraction of a muscle of the organism having the innate immune mechanism by the innate immunity activation substance, or not; and
(c') a step of selecting a substance evaluated to suppress the contraction of the muscle of the organism having the innate immune mechanism;
(d') a step of generating the substance selected in the step (c'); and
(e') a step of mixing the substance generated in the step (d') and a pharmaceutically acceptable carrier (second drug production method).

<20> A method of producing a food having an action of suppressing an innate immune mechanism, comprising
(a') a step of administering a material to be tested and an innate immunity activation substance to an organism having the innate immune mechanism;
(b') a step of evaluating whether the material to be tested suppresses a contraction of a muscle of the organism having the innate immune mechanism by the innate immunity activation substance, or not;
(c') a step of selecting a substance evaluated to suppress the contraction of the muscle of the organism having the innate immune mechanism;
(d') a step of generating the substance selected in the step (c'); and
(e') a step of mixing the substance generated in the step (d') and a food raw material (second food production method).

<21> An innate immunity suppressor comprising a substance having an action of suppressing a contraction of a muscle of an organism having an innate immune mechanism as an active ingredient.

<22> A food having an action of suppressing an innate immunity, comprising a substance having an action of suppressing a contraction of a muscle of an organism having an innate immune mechanism.

Effect of the Invention

According to the present invention, the conventional various problems can be solved, the substance that has problems for pharmaco-kinetics in the individual can be excluded, and no effect of lipopolysaccharide (LPS) derived from the bacteria, which can be contaminated during the search is given. That is, according to the present invention, it is possible to detect the innate immunity activation substance other than LPS because no LPS is reacted. Also the evaluation method and the screening method capable of simply and easily searching the substance having the action of activating/suppressing the innate immune mechanism, as well as the drug and the food for activating/suppressing the innate immune mechanism, and the methods of producing the same can be provided.

BRIEF DESCRIPTION OF DRAWINGS

FIG. 7 is a view showing that LPS derived from bacteria caused no muscular contraction in the silkworm larvae;

BEST MODES FOR CARRYING OUT THE INVENTION

Figure 1:
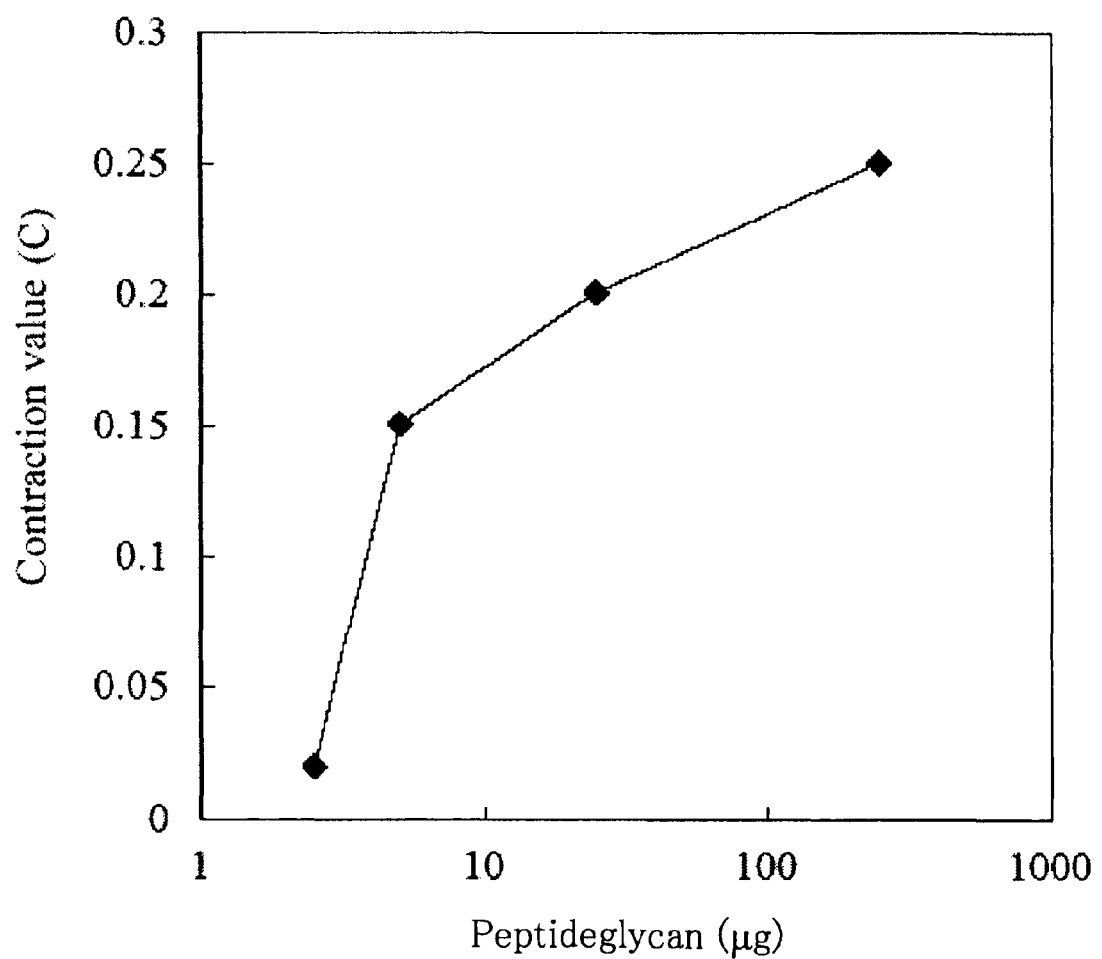
FIG. 1 is a graph showing muscular contraction induced by peptideglycan in silkworm larvae.

First Evaluation Method and First Screening Method

The first evaluation method of the present invention is the method of evaluating whether a material to be tested has the action of activating the innate immune mechanism or not, comprises the following steps (a) to (b) and further comprises other steps if necessary.

The first screening method of the present invention is the method of screening a substance having the action of activating the innate immune mechanism, comprises the following steps (a) to (c) and further comprises the other steps if necessary.

Hereinafter, the first evaluation method and the first screening method are sometimes collectively referred to as a "first method" simply.

<Step (a)>

In the first method, the material to be tested is administered to an organism having the innate immune mechanism (step (a)).

—Organism Having Innate Immune Mechanism—

The screening method of the present invention is based on the finding that the innate immune mechanism is closely associated with the muscular contraction mechanism by the aforementioned mechanism. Thus the "organism having the innate immune mechanism is not particularly limited as long as the muscle is contracted in response to the activation of the innate immunity, and can be appropriately selected from any multicellular organisms depending on the purpose. As long as the activation of the innate immunity can be evaluated using the muscular contraction as the indicator, life or death of an individual is no object.

In the present invention, among the organisms having the innate immune mechanism, in particular, it is preferable to use the organism having the innate immune mechanism alone. The "innate immune mechanism" means an immune body defense mechanism (congenital immune mechanism) not depending on the acquired immunity (acquired immunity) mechanism. Vertebrate animals have the acquired immune mechanism in which the body is protected against an invaded pathogen utilizing a molecule such as an antibody that specifically recognizes the invader, but invertebrate animals do not have such an acquired immune mechanism. That is, the "organism having the innate immune mechanism alone" is, in other words, the invertebrate animal having no acquired immune mechanism.

Therefore, the "organism having the innate immune mechanism alone" can be appropriately selected from the invertebrate animals depending on the purpose, but among them, the organism belonging to the insects is preferable. The "insects" means a class that is one class of Arthropoda Mandibulata and is composed of four subclasses, i.e., Protura, Collembola, wingless insects and winged insects.

The "organism belonging to the insects" is not particularly limited and can be appropriately selected depending on the purpose, but it is preferable to be a larva in terms of convenience in handling. The larva is not particularly limited and can be appropriately selected depending on the purpose, and includes larvae of Lepidoptera (including night flies and butterflies) and Coleoptera (including beetles). The larva is preferably the large size larva in terms of easy administration of the material to be tested. The large size larva indicates the larva having a body length of 1 cm or more. As the larva, for example, the larvae of a silkworm (silkworm moth) and erisan (*Philosamia cynthia ricini*) are preferable.

As the organism having the innate immune mechanism, it is preferable to use the organism in which the muscular contraction by the material to be tested is easily measured, and in this point, the silkworm larva is particularly suitable. As the silkworm larva, it is preferable to use an isolated head muscle specimen of the silkworm larva as shown in Examples described later. It is advantageous to use the isolated head muscle specimen of the silkworm larva in that input of signals from a nerve center can be excluded.

—Materials to be Tested—

The "material to be tested" is not particularly limited, and any substance to be evaluated on whether the substance has the action of activating the innate immune mechanism or not can be used. Examples thereof include cell extracts, cultured cell supernatants, fermentation microorganism products, marine organism extracts, plant extracts, microorganism extracts, purified proteins, crude purified proteins, peptides, non-peptidic compounds, artificially synthesized compounds, naturally occurring compounds and known innate immunity activators.

—Administration—

The method of administering the material to be tested to the organism having the innate immune mechanism is not particularly limited, can be appropriately selected depending on the purpose, and includes, for example, an oral administration, an intraperitoneal administration, an injection into blood, an injection into intestine and an addition to feedstuffs.

A dosage of the material to be tested administered to the organism having the innate immune mechanism is not particularly limited, and can be appropriately selected depending on the purpose.

<Step (b)>

In the first method, it is evaluated whether the material to be tested contracts the muscle of the organism having the innate immune mechanism or not (step (b)).

The method of evaluating whether the material to be tested contracts the muscle of the organism having the innate immune mechanism or not is not particularly limited, and can be appropriately selected depending on the purpose. For example, it is possible to evaluate by representing the degree of the muscular contraction of the organism having the innate immune mechanism by a contraction value (C value) (e.g., see Sekimizu et al., J. Biochem., 137:199-203, 2005). Specifically, the body length of the organism having the innate immune mechanism before and after the administration of the material to be tested is measured. Then, the value (C value) is calculated by dividing "[Body length before administration]−[Body length after administration]" by "[Body length before administration]". The larger the degree of the muscular contraction is, the larger the C value is. When the muscle is not contracted at all, the C value is zero. Conversely if the muscle is relaxed, the C value becomes a negative value. A process of the muscular contraction is monitored by an appropriate method, e.g., using a transducer linked to a recorder, and it is adequate to measure the C value when the degree of the muscular contraction is maximized. A period of time required for the muscular contraction varies depending on a type and an amount of the administered material to be tested. Thus it is desirable to appropriately select the period of time.

When the C value is a positive value, the material to be tested can be evaluated to contract the muscle of the organism having the innate immune mechanism. The larger the C value is, the action of the material to be tested to contract the muscle of the organism having the innate immune mechanism can be evaluated to be stronger.

When the material to be tested was evaluated to contract the muscle of the organism having the innate immune mechanism in the step (b), the material to be tested can be evaluated to have the action of activating the innate immune mechanism. The stronger the action of the material to be tested to contract the muscle of the organism having the innate immune mechanism is, the action of the material to be tested to activate the innate immune mechanism can be evaluated to be stronger.

As described above, the first evaluation method can be carried out by the step (a) and the step (b). By the first evaluation method, it can be easily and efficiently evaluated whether the material to be tested has the action of activating the innate immune mechanism or not.

<Step (c)>

In the first screening method, further the substance evaluated to contract the muscle of the organism having the innate immune mechanism in the step (b) is selected (step (c)).

The substance having the action of activating the innate immune mechanism can be easily and efficiently screened by performing the evaluation in the steps (a) and (b) using various materials to be tested and then selecting the substance evaluated to contract the muscle of the organism having the innate immune mechanism from various materials to be tested in the step (c).

Second Evaluation Method and Second Screening Method

The second evaluation method of the present invention is the method of evaluating whether the material to be tested has the action of suppressing the innate immune mechanism or not, comprises the following steps (a') and (b'), and further comprises the other steps if necessary.

The second screening method of the present invention is the method of screening the substance having the action of suppressing the innate immune mechanism, comprises the following steps (a') to (c'), and further comprises the other steps if necessary.

Hereinafter, the second evaluation method and the second screening method are sometimes collectively referred to as a "second method" simply.

<Step (a')>

In the second method, the material to be tested and the innate immunity activation substance are administered to the organism having the innate immune mechanism (Step (a')).

—Organism Having the Innate Immune Mechanism—

The organism having the innate immune mechanism is the same as in the first method of the present invention described above.

—Materials to be Tested—

The "material to be tested" is not particularly limited, and any substance to be evaluated on whether the substance has the action of suppressing the innate immune mechanism or not can be used. Examples thereof include cell extracts, cultured cell supernatants, fermentation microorganism products, marine organism extracts, plant extracts, microorganism extracts, purified proteins, crude purified proteins, peptides, non-peptidic compounds, artificially synthesized compounds, naturally occurring compounds and known innate immunity suppressors.

—Innate Immunity Activation Substance—

The innate immunity activation substance is not particularly limited, can be appropriately selected depending on the purpose, and for example, the known innate immunity activation substance can be used. Specifically, for example, peptideglycan, β-glucan, and killed bacteria and fungi containing them are included.

It is preferable that the innate immunity activation substance is the substance that can induce the muscular contraction of the organism having the innate immune mechanism. The muscular contraction of the organism having the innate immune mechanism is induced by the innate immunity activation substance, thereby being capable of evaluating whether the material to be tested suppresses the muscular contraction of the organism having the innate immune mechanism or not in the step (b') described later.

As the innate immunity activation substance, the substance evaluated to have the action of activating the innate immune mechanism in the first method of the present invention described above may be used.

—Administration—

The method of administering the material to be tested and the innate immunity activation substance to the organism having the innate immune mechanism is the same as in the first method of the present invention described above. The dosages of the material to be tested and the innate immunity activation substance to be administered to the organism having the innate immune mechanism are not particularly limited, and can be appropriately selected depending on the purpose.

<Step (b')>

In the second method, it is evaluated whether the material to be tested suppresses the muscular contraction of the organism having the innate immune mechanism, induced by the innate immunity activation substance (step (b')).

The method of evaluating whether the material to be tested suppresses the muscular contraction of the organism having the innate immune mechanism, induced by the innate immunity activation substance is not particularly limited, and can be appropriately selected depending on the purpose. For example, it is possible to evaluate by representing the degree of the muscular contraction of the organism having the innate immune mechanism by the contraction value (C value) (e.g., see Sekimizu et al., J. Biochem., 137:199-203, 2005) in the same manner as in the first method of the present invention described above. How to calculate the C value is the same as in the first method of the present invention described above.

More specifically, first the material to be tested is administered to the organism having the innate immune mechanism, and then the innate immunity activation substance is administered to cause the muscular contraction in the step (a'). The C value when both the material to be tested and the innate immunity activation substance were administered to the organism having the innate immunity mechanism, and the C value when the material to be tested was not administered and the innate immunity activation substance alone was administered are obtained, respectively. When the C value when both the material to be tested and the innate immunity activation substance were administered is smaller than the C value when the innate immunity activation substance alone was administered, the material to be tested can be evaluated to suppress the muscular contraction of the organism having the innate immune mechanism. The larger the difference between the C value when both the material to be tested and the innate immunity activation substance were administered and the C value when the innate immunity activation substance alone was administered is, the action of the material to be tested that suppresses the muscular contraction of the organism having the innate immune mechanism can be evaluated to be stronger.

When the material to be tested is evaluated to suppress the muscular contraction of the organism having the innate immune mechanism in the step (b'), the material to be tested can be evaluated to have the action of suppressing the innate immune mechanism. The stronger the action of the material to be tested that suppresses the muscular contraction of the organism having the innate immune mechanism is, the action of the material to be tested that suppresses the innate immune mechanism can be evaluated to be stronger.

As described above, the second evaluation method can be carried out by the steps (a') and the steps (b'). By the second evaluation method, it can be easily and efficiently evaluated whether the material to be tested has the action of suppressing the innate immune mechanism or not.

<Step (c')>

In the second screening method, further the substance evaluated to suppress the muscular contraction of the organism having the innate immune mechanism in the step (b') is selected (step (c')).

The evaluation is carried out using various materials to be tested by the steps (a') and (b'). Then, in the step (c'), by selecting the substance evaluated to suppress the muscular contraction of the organism having the innate immune mechanism from various materials to be tested, it is possible to easily and efficiently screen the substance having the action of suppressing the innate immune mechanism.

Both the first method and the second method are characterized in that the evaluation or the screening of the substance having the action of regulating (activating/suppressing) the innate immune mechanism is performed using the muscular contraction of the organism such as silkworm larvae having the innate immune mechanism as the indicator.

Here, the substance having the action of regulating (activating/suppressing) the innate immune mechanism in the first method and the second method is preferably the substance having the action of regulating (activating/suppressing) the innate immune mechanism in mammalian animals, and more preferably the substance having the action of regulating (activating/suppressing) the innate immune mechanism in human beings. According to the first method and the second method, for example using the silkworm larvae, it becomes possible to easily and efficiently evaluate or screen the substance having the action of regulating (activating/suppressing) the innate immune mechanism in the mammalian animals, e.g., the human beings.

The substance evaluated or screened in the first method and the second method and having the action of regulating (activating/suppressing) the innate immune mechanism can be appropriately generated by a technique such as chemical synthesis or isolation and purification. Intended uses of the substance are not particularly limited, can be appropriately selected depending on the purpose, and the substance can be used for treatment, improvement or prevention of diseases due to the abnormal innate immune mechanism, directly or by appropriately processing. The substance can also be used for the drug produced by the first drug production method/the second drug production method and the food produced by the first food production method/the second food production method of the present invention described later, and the innate immunity activator and the food of the present invention described later.

First Drug Production Method/First Food Production Method

The first drug production method and the first food production method are the methods of producing the drug for activating the innate immune mechanism and the food having the action of activating the innate immune mechanism, both the methods comprise the following step (a) to step (e) and further comprise the other steps if necessary.

<Step (a) to Step (c)>

The step (a) to the step (c) in the first drug production method and the first food production method are the same as the step (a) to the step (c) in the first method of the present invention described above. By the step (a) to the step (c), it is possible to easily and efficiently select the substance having the action of activating the innate immune mechanism.

<Step (d)>

Then, the substance selected in the steps (a) to (c) and having the action of activating the innate immune mechanism is generated in the first drug production method and the first food production method (step (d)).

Means for the generation is not particularly limited, and can be appropriately selected from publicly known generation means such as chemical synthesis and isolation/purification depending on a structure and a source of the substance.

<Step (e)>

Then, the substance generated in the step (d) is mixed with a pharmaceutically acceptable carrier or a food raw material in the first drug production method and the first food production method (step (e)).

—Pharmaceutically Acceptable Carrier—

The pharmaceutically acceptable carrier in the first drug production method is not particularly limited, and can be appropriately selected depending on, for example, a desired dosage form of the drug to be produced. The dosage form is also not particularly limited, and includes the dosage forms listed in a section of the innate immunity activator/innate immunity suppressor of the present invention described later.

—Food Raw Material—

The food raw material in the first food production method is not particularly limited, and can be appropriately selected depending on, for example, a kind of the food to be produced. The kinds of the foods are also not particularly limited, and include the foods listed in a section of the foods of the present invention described later.

—Immixture—

The method of mixing the substance generated in the step (d) and the pharmaceutically acceptable carrier or the food raw material is not particularly limited, and for example, can be appropriately selected from the methods of mixing the respective ingredients in the publicly known drug production methods or the publicly known food production methods. A dose ratio of the substance to the pharmaceutically acceptable carrier or the food raw material when mixed is not particularly limited, and can be appropriately selected depending on the purpose.

<Other Steps>

The other steps are not particularly limited, can be appropriately selected depending on the purpose, and include, for example, a step of molding the mixture obtained in the step (e) and the like.

As described above, by the step (a) to the step (e), it is possible to perform the first drug production method and the first food production method of the present invention. This makes it possible to efficiently produce the drug for activating the innate immune mechanism, and the food having the action of activating the innate immune mechanism. A use form of the drug and the food obtained by the first drug production method and the first food production method is not particularly limited, can be appropriately selected depending on the purpose, and the drug and the food can be used in the same form as in the innate immunity activator and the food having the action of activating the innate immune mechanism of the present invention described later.

Second Drug Production Method and Second Food Production Method

The second drug production method and the second food production method are the methods of producing the drug for suppressing the innate immune mechanism and the food having the action of suppressing the innate immune mechanism, both the methods comprise the following step (a') to step (e') and further comprise the other steps if necessary.

<Step (a') to Step (c')>

The step (a') to the step (c') in the second drug production method and the second food production method are the same as the step (a') to the step (c') in the second method of the present invention described above. By the step (a') to the step (c'), it is possible to easily and effectively select the substance having the action of suppressing the innate immune mechanism.

<Step (d') to Step (e')>

In the second drug production method and the second food production method, then the substance selected in the steps (a') to (c') and having the action of suppressing the innate immune mechanism is generated (step (d'). Further, the substance generated in the step (d') is mixed with the pharmaceutically acceptable carrier or the food raw material (step (e')).

The step (d') to the step (e') in the second drug production method and the second food production method can be carried out in the same manner as in the step (d') to the step (e') in the first drug production method and the first food production method of the present invention as described above.

<Other Steps>

The other steps can be carried out in the same manner as in the first drug production method and the first food production method of the present invention as described above.

As described above, by the step (a') to step (e'), it is possible to perform the second drug production method and the second food production method of the present invention. This makes it possible to efficiently produce the drug for suppressing the innate immune mechanism, and the food having the action of suppressing the innate immune mechanism. The use form of the drug and the food obtained by the second drug production method and the second food production method is not particularly limited, can be appropriately selected depending on the purpose, and the drug and the food can be used in the same form as in the innate immunity suppressor and the food having the action of suppressing the innate immune mechanism of the present invention described later.

Innate Immunity Activator and the Food Having the Action of Activating the Innate Immune Mechanism The innate immunity activator and the food having the action of activating the innate immune mechanism in the present invention contain the substance having the action of contracting the muscle of the organism having the innate immune mechanism, and further contain other ingredients and raw materials if necessary. The innate immunity activator and the food having the action of activating the innate immune mechanism may be those produced by the first drug production method and the first food production method of the present invention described above.

—Substance Having the Action of Contracting the Muscle of the Organism Having the Innate Immune Mechanism—

The "organism having the innate immune mechanism" is the same as in the first method of the present invention described above.

The substance having the action of contracting the muscle of the organism having the innate immune mechanism is not particularly limited, can be appropriately selected depending on the purpose, and includes, for example, extracts and purified products of vegetables such as carrots, burdocks, cilantro leaves, bell peppers, broccolis, and turmeric, gooey components of fermented soybeans and lyophilized products thereof, extracts of various Chinese herbal medicines and galenicals. Among them, the extract and the purified product of the turmeric are preferable as the substance having the action of contracting the muscle of the organism having the innate immune mechanism. The method of extracting or purifying the turmeric is not particularly limited, can be appropriately selected, and includes suitably, for example, the methods described in Examples. The various extracts are preferably the extracts with hot water. The extract by boiling under applied pressure is one of particularly preferable aspects.

As the substance having the action of contracting the muscle of the organism having the innate immune mechanism, it is also possible to use the substance evaluated and screened to activate the innate immune mechanism in the first method of the present invention described above.

—Aspects in Innate Immunity Activator—

A content of the substance (active ingredient) having the action of contracting the muscle of the organism having the innate immune mechanism in the innate immunity activator is not particularly limited, can be appropriately selected depending on the purpose, and the innate immunity activator may be the active ingredient itself.

The substance (active ingredient) having the action of contracting the muscle of the organism having the innate immune mechanism may be used alone or in combination of two or more. When two or more substances are combined, a content ratio of the respective active ingredients in the innate immunity activator is not particularly limited, and can be appropriately selected depending on the purpose.

The other ingredient in the innate immunity activator is not particularly limited, can be appropriately selected depending on the purpose within the range in which the effects of the present invention are not impaired, and includes, for example, the pharmaceutically acceptable carrier. The carrier is not particularly limited, can be appropriately selected depending on the dosage form of the drug described later. The content of the other ingredient in the innate immunity activator is not particularly limited, and can be appropriately selected depending on the purpose The dosage form of the innate immunity activator is not particularly limited, and can be appropriately selected depending on, for example, the desired administration method as described later, and includes, for example, oral solid agents (tablets, coated tablets, granules, powders, capsules), oral liquid agents (liquid agent for internal use, syrup agents, elixir agents), injectable agents (solutions, suspensions, solid agents to be dissolved in use), ointments, patches, gel agents, cream agents, powders for external use, spray agents and powders for inhalation.

The oral solid agents can be produced, for example, by adding an excipient to the active ingredient, and further if necessary adding additives such as a binder, a disintegrant, a lubricant, a coloring agent, and a flavoring agent thereto and by a standard method.

The excipient includes, for example, lactose, saccharose, sodium chloride, glucose, starch, calcium carbonate, kaolin, fine crystalline cellulose and silic acid. The binder includes, for example, water, ethanol, propanol, simple syrup, a glucose solution, a starch solution, a gelatin solution, carboxymethylcellulose, hydroxypropylcellulose, hydroxypropyl starch, methylcellulose, ethylcellulose, shellac, calcium phosphate and polyvinyl pyrrolidone. The disintegrant includes, for example, dry starch, sodium alginate, agar powder, sodium hydrogen carbonate, calcium carbonate, sodium lauryl sulfate, monoglyceride stearate and lactose. The lubricant includes, for example, purified talc, stearate salts, borax and polyethylene glycol. The coloring agent includes, for example, titanium oxide and iron oxide. The flavoring agents include, for example, saccharose, orange peel, citric acid and tartaric acid.

The oral liquid agent can be produced, for example, by adding the additives, e.g., the flavoring agent, a buffer and a stabilizer to the active ingredient and by the standard method.

The flavoring agents include, for example, saccharose, orange peel, citric acid and tartaric acid. The buffer includes, for example, sodium citrate. The stabilizer includes, for example, tragacanth, gum arabic and gelatin.

The injectable agents for subcutaneous, intramuscular and intravenous injections can be produced by the standard method, for example, by adding a pH adjuster, the buffer, the stabilizer, a tonicity agent and a local anesthetic to the active ingredient.

The pH adjuster and the buffer include, for example, sodium citrate, sodium acetate and sodium phosphate. The stabilizer includes, for example, sodium pyrosulfite, EDTA, thioglycolic acid and thiolactic acid. The tonicity agent includes, for example, sodium chloride and glucose. The local anesthetic includes, for example, procaine hydrochloride and lidocaine hydrochloride.

The ointment can be produced by combining a publicly known base, the stabilizer, a wetting agent and a preservative with the active ingredient and mixing them by the standard method The base includes, for example, liquid paraffin, white petrolatum, refined bee wax, octyldodecyl alcohol and paraffin. The preservative includes, for example, methyl paraoxybenzoate, ethyl paraoxybenzoate and propyl paraoxybenzoate.

The patch can be produced by applying the cream agent, the gel agent or the paste agent as the ointment on a publicly known support by the standard method. The support includes, for example, cottons, staple fibers, wovens and nonwovens composed of chemical fibers, films of soft vinyl chloride, polyethylene and polyurethane, and foam sheets.

The innate immunity activator can be used by administering it to individuals who require the activation of the innate immune mechanism (e.g., the individuals who require health maintenance and recovery from fatigue, the individuals who require the prevention or the treatment of cancers or lifecycle related diseases and the individuals infected with bacteria, fungi or viruses).

Animals subjected to the administration of the innate immunity activator is not particularly limited, can be appropriately selected depending on the purpose, and include, for example, human beings, mice, rats, cattle, swines and monkeys.

The method of administering the innate immunity activator is not particularly limited, can be appropriately selected depending on the dosage form of the innate immunity activator, and includes oral administration, intraperitoneal administration, injection into the blood and injection into the intestine.

A dosage of the innate immunity activator is not particularly limited, can be appropriately selected depending on an age, a body weight and a degree of desired effects in a patient to be administered, and for example, is preferably 1 mg to 10 g and more preferably 10 mg to 1 g as the active ingredient per day for an adult.

An administration period of the innate immunity activator is not particularly limited, can be appropriately selected depending on the purpose, and for example, may be administered preventively or may be administered therapeutically.

—Aspects in Food Having Action of Activating Innate Immunity—

The content of the substance having the action of contracting the muscle of the organism having the innate immune mechanism in the food having the action of activating innate immunity is not particularly limited, can be appropriately selected depending on the purpose, and the food having the action of activating innate immunity may be the substance itself having the action of contracting the muscle of the organism having the innate immune mechanism.

The substance having the action of contracting the muscle of the organism having the innate immune mechanism may be used alone or in combination of two or more. When two or more substances are combined, the content ratio of the respective substances in the food is not particularly limited, and can be appropriately selected depending on the purpose.

The other ingredient in the food having the action of activating the innate immunity is not particularly limited, can be appropriately selected depending on the purpose within the range in which the effects of the present invention are not impaired, and includes, for example, various food raw materials.

The kinds of the foods are not particularly limited, can be appropriately selected depending on the purpose, and include, for example, sweet snacks such as jellies, candies, chocolates and biscuits, taste beverages such as green tea, black tea, coffee and soft drinks, milk products such as raw material milks, yogurts and ice creams, processed vegetable and fruit products such as vegetable beverages, fruit beverages and jams, liquid foods such as soups, processed grain products such as breads and noodles, and various seasonings. The method of producing these foods is not particularly limited, and can be appropriately produced depending on, for example, the method of producing the ordinary various foods.

The foods may be those produced as the oral solid agents, e.g., the tablet, the granule and the capsule, and the oral liquid agents, e.g., the liquid agent for internal use and the syrup agent. The method of producing the oral solid agent and the oral liquid agent is not particularly limited, can be appropriately selected depending on the purpose, and can be produced, for example, according to the method of producing the oral solid agent and the oral liquid agent of the drugs described above.

It is believed that the food is particularly useful as a functional food or a health food for the purpose of activating the innate immune mechanism.

The content of the other ingredient in the food is not particularly limited, and can be appropriately selected depending on the purpose.

Innate Immunity Suppressor and Food Having Action of Suppressing Innate Immunity The innate immunity suppressor and the food having the action of suppressing the innate immunity of the present invention contain the substance having the action of suppressing the contraction of the muscle of the organism having the innate immune mechanism, and further contain the other ingredients if necessary. The innate immunity suppressor and the food having the action of suppressing the innate immunity may be those produced by the second drug production method and the second food production method.

—Substance Having the Action of Suppressing the Contraction of the Muscle of the Organism Having the Innate Immune Mechanism—

The "organism having the innate immune mechanism" is the same as in the first method of the present invention described above.

The substance having the action of suppressing the contraction of the muscle of the organism having the innate immune mechanism is not particularly limited, can be appropriately selected depending on the purpose, and the substance evaluated and screened to suppress the innate immune mechanism in the second method of the present invention described above can be used.

—Aspects in Innate Immunity Suppressor—

The content of the substance (active ingredient) having the action of suppressing the contraction of the muscle of the organism having the innate immune mechanism in the innate immunity suppressor is not particularly limited, can be appropriately selected depending on the purpose, and the innate immunity suppressor may be the active ingredient itself.

The substance (active ingredient) having the action of suppressing the contraction of the muscle of the organism having the innate immune mechanism may be used alone or in combination of two or more. When two or more substances are combined, the content ratio of the respective active ingredients in the innate immunity suppressor is not particularly limited, and can be appropriately selected depending on the purpose.

The other ingredients in the innate immunity suppressor are the same as the other ingredients in the innate immunity activator of the present invention described above. The dosage form of the innate immunity suppressor is the same as the dosage form in the innate immunity activator of the present invention described above.

The innate immunity suppressor can be used by administering it to the individuals who require the suppression of the innate immune mechanism (e.g., the individuals who require the prevention of a reject reaction against a transplanted organ, the individuals who require the prevention or the treatment of an autoimmune disease, and the individuals having abnormally promoted innate immunity due to the infection with bacteria or fungi).

The animals subjected to the administration of the innate immunity suppressor is not particularly limited, can be appropriately selected, and include, for example, human beings, mice, rats, cattle, swines and monkeys.

The method of administering the innate immunity suppressor is not particularly limited, can be appropriately selected depending on the dosage form of the drug, and includes the oral administration, the intraperitoneal administration, the injection into the blood and the injection into the intestine.

The dosage of the innate immunity suppressor is not particularly limited, can be appropriately selected depending on the age, the body weight and the degree of desired effects in the patient to be administered, and for example, is preferably 1 mg to 10 g and more preferably 10 mg to 1 g as the active ingredient per day for the adult.

An administration period of the innate immunity suppressor is not particularly limited, can be appropriately selected depending on the purpose, and for example, may be administered preventively or may be administered therapeutically.

—Aspects in Food Having Action of Suppressing Innate Immunity—

The content of the substance having the action of suppressing the contraction of the muscle of the organism having the innate immune mechanism in the food having action of suppressing innate immunity is not particularly limited, can be appropriately selected depending on the purpose, and the food having action of suppressing innate immunity may be the substance itself having the action of suppressing the contraction of the muscle of the organism having the innate immune mechanism.

The substance having the action of suppressing the contraction of the muscle of the organism having the innate immune mechanism may be used alone or in combination of two or more. When two or more substances are combined, the content ratio of the respective substances in the food is not particularly limited, and can be appropriately selected depending on the purpose.

The other ingredients in the food having the action of suppressing the innate immunity are the same as the other ingredients in the food having the action of activating the innate immunity of the present invention described above.

The kinds of the food having the action of suppressing the innate immunity are the same as the kinds in the food having the action of activating the innate immunity of the present invention described above.

It is believed that the food is particularly useful as the functional food or the health food for the purpose of suppressing the innate immune mechanism.

EXAMPLES

Examples of the present invention will be described below, but the present invention is not limited to these Examples.

Example 1

Muscular Contraction of Silkworm Larva by Peptideglycan or β-Glucan

It has been already known that peptideglycan derived from bacteria and β-glucan derived from mushrooms have the action of activating the innate immune system (innate immune mechanism) (e.g., see Adachi & Ohno, "Recognition of fungal polysaccharide by immune system and its activation effect", Jpn. J. Med. Mycol., 47, 185-194, 2006 and Akira, S., Uematsu, S., and Takeuchi O., Pathogen recognition and innate immunity., Cell, 124, 783-801, 2006). In this Example, the effect of these innate immunity activation substances on the muscular contraction in the silkworm larva was examined.
<Method>

Peptideglycan derived from *Staphylococcus aureus* (Sigma) or β-glucan derived from the mushroom (an extract from *Agaricus* mushroom with hot water was used in this Example) was suspended in 0.9% NaCl, then 0.05 mL thereof was injected in a body cavity of an isolated head muscle specimen of the silkworm larva (see Sekimizu et al., J. Biochem., 137:199-203, 2005) using a 1 mL disposable syringe (Terumo), and a body length when the maximum contraction was exhibited after the injection (after about 10 minutes) was measured.

A degree of the muscular contraction of the silkworm larva was evaluated by a contraction value (C value) (see Sekimizu et al., J. Biochem., 137:199-203, 2005). Here, the C value is the value calculated by dividing "[Body length (cm) before administration]−[Body length (cm) after administration]" by "[Body length (cm) before administration]". The larger the degree of the muscular contraction is, the larger the C value is. When the muscle is not contracted at all, the C value is zero. Conversely if the muscle is relaxed, the C value becomes a negative value. The value when saline (0.9% NaCl) alone had been injected was zero. When the muscle is contracted maximally under an ordinary experiment condition, the C value is 0.4.

Also, 0.05 mL of a solution in which L-glutamic acid (40 mM) had been previously dissolved in 0.9% NaCl was injected in the isolated head muscle specimen of the silkworm larva, then immediately 0.05 mL of the suspension of 0.5 mg/mL or 5 mg/mL peptideglycan derived from *Staphylococcus aureus* was injected, and the body length when the maximum contraction was exhibited (after about 10 minutes) was measured and the C value was calculated. The experiment using kainic acid (0.2 mM) in place of peptideglycan was carried out as a control experiment. It has been known that kainic acid is an agonist of a glutamic acid receptor and induces the muscular contraction by strongly binding to a glutamine receptor to excessively stimulate the nerve. It has been already known that the muscular contraction induced by kainic acid is inhibited by L-glutamic acid.
<Results>

Figure 2:
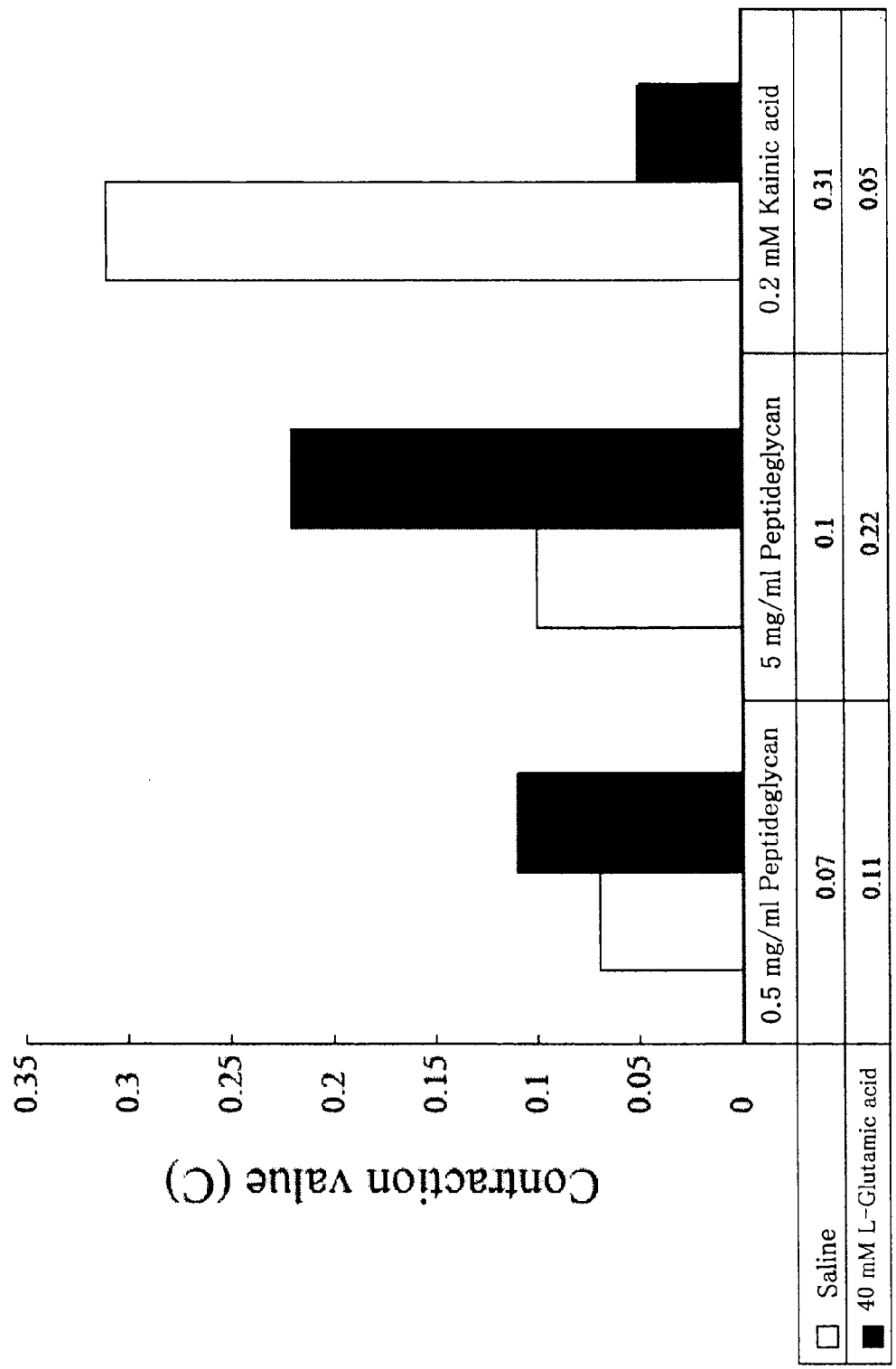
FIG. 2 is a graph showing effects of L-glutamic acid on the muscular contraction induced by peptideglycan in the silkworm larvae.

The results are shown in FIGS. 1 and 2.

When each dose of the innate immunity activation substances (peptideglycan derived from *Staphylococcus aureus* and β-glucan derived from the mushroom) was injected into the isolated head muscle specimen of the silkworm larva, both the substances induced the muscular contraction (FIG. 1). A time period that gave a half contraction of the maximum muscular contraction ($t_{1/2}$ value) was within 2 seconds in the case of kainic acid, while the $t_{1/2}$ value was 2 minutes or longer in the cases of peptideglycan and β-glucan. Further, the muscular contraction of the silkworm larva induced by kainic acid was inhibited by L-glutamic acid, but the muscular contraction of the silkworm larva induced by peptideglycan and β-glucan was not inhibited by L-glutamic acid (FIG. 2).

From the results in this Example, it was shown that the innate immunity activation substances such as peptideglycan and β-glucan had the action of inducing the muscular contraction in the silkworm larva. This suggests that the innate immune mechanism and the muscular contraction mechanism are associated and work in the organisms such as silkworm larvae having the innate immune mechanism.

It has been also generally known that the muscular contraction is induced by stimulating the nerve with a neurotransmitter such as D-glutamic acid and kainic acid (agonist of glutamic acid receptor), and it has been known that the muscular contraction through such a neurotransmitter is inhibited by L-glutamic acid. On the contrary, from the results in this Example, it was shown that the muscular contraction by the innate immunity activation substances such as peptideglycan and β-glucan was not inhibited by L-glutamic acid. This suggests the mechanism in which these innate immunity activation substances induce the muscular contraction through a different pathway from those of D-glutamic acid and kainic acid.

Example 2

Muscular Contraction by Silkworm (*Bombyx mori*) Paralytic Peptide BmPP in Silkworm Larvae It has been known that when a body fluid is removed from a silkworm larva and the body fluid is further injected into the silkworm larva again, the silkworm larva is paralyzed. This paralytic substance is a peptide referred to as BmPP composed of 24 amino acid residues (see Ha et al., Peptides, 20, 561-568, 1999). In this Example, a synthetic product of this peptide was injected into the isolated head muscle specimen of the silkworm larvae, and its reaction was examined.
<Method>
BmPP (provided by Dr. Manabu Kamimura, National Institute Agrobiological Sciences) at various concentrations were dissolved in 0.9% NaCl, 0.05 mL thereof was injected in the body cavity of the isolated head muscle specimen of the silkworm larva, the body length was measured after 6 minutes, and the C value was calculated in the same manner as in Example 1.

Also, 0.05 mL of the solution in which L-glutamic acid (40 mM) had been previously dissolved in 0.9% NaCl was injected, then immediately BmPP was injected, and the body length when the maximum contraction was exhibited (after about 10 minutes) was measured and the C value was calculated. The experiment using kainic acid (0.2 mM) in place of BmPP was carried out as the control experiment.
<Results>
The results are shown in FIGS. 3 and 4.

Figure 3:
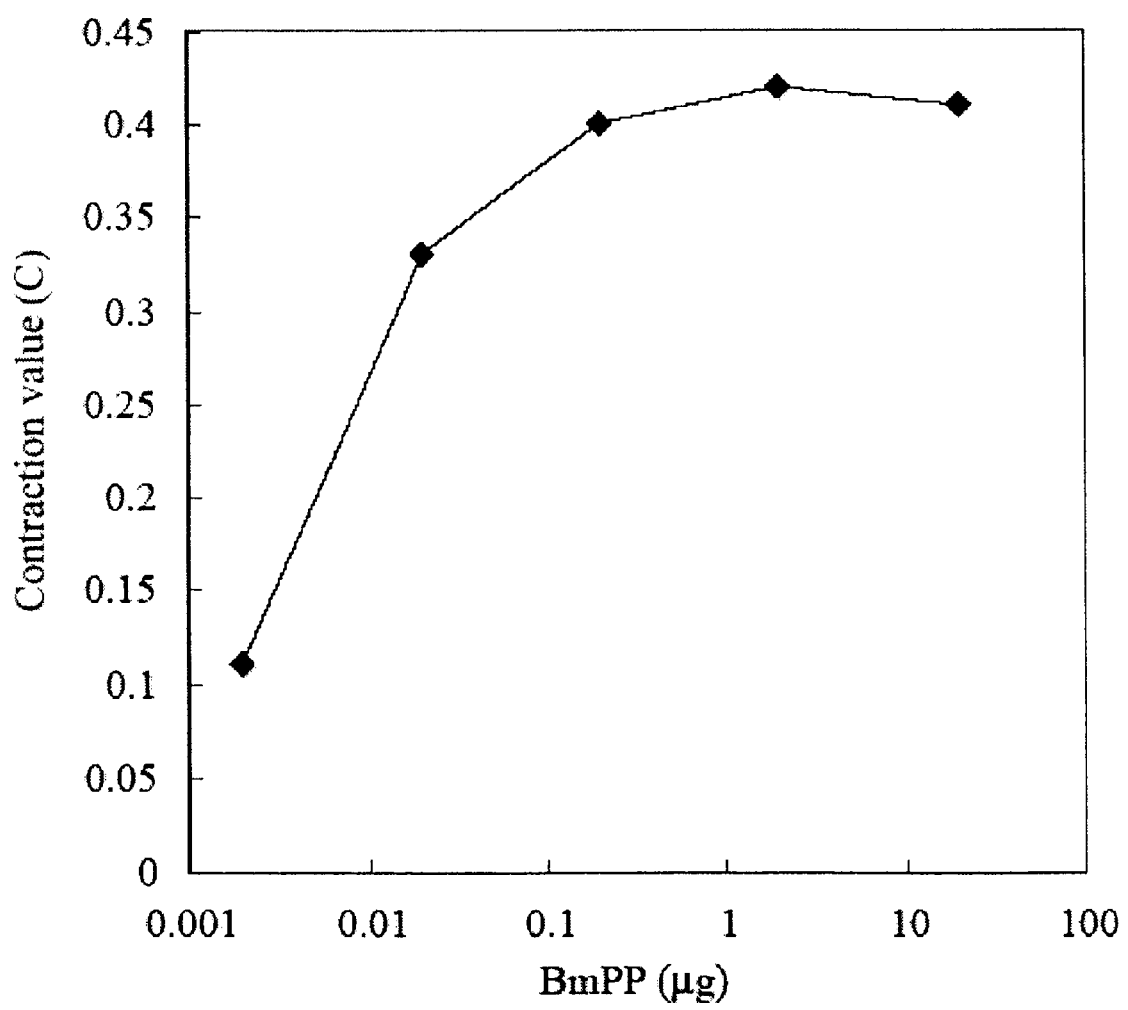
FIG. 3 is a graph showing the muscular contraction induced by BmPP in silkworm larvae.
Figure 4:
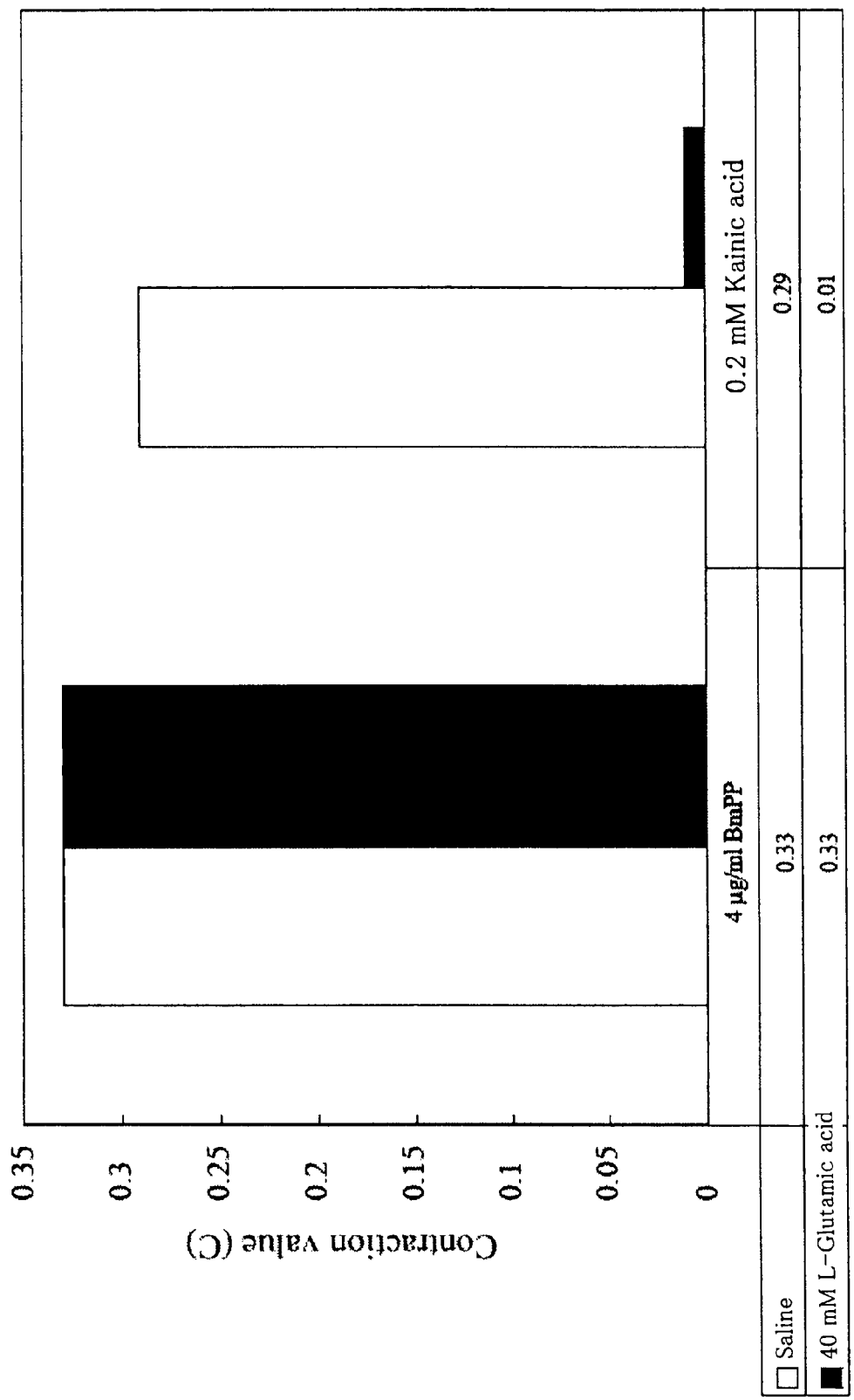
FIG. 4 is a graph showing the effects of L-glutamic acid on the muscular contraction induced by BmPP in the silkworm larvae.

It was found that when BmPP was injected in the isolated head muscle specimen of the silkworm larva, 10 ng of BmPP caused the muscular contraction (FIG. 3). When this amount of BmPP is injected in the alive silkworm larva, the paralysis is caused. Therefore, it is conceivable that the paralysis in the silkworm larva occurs due to the muscular contraction.

The $t_{1/2}$ value of the muscular contraction induced by BmPP is 2 minutes or longer. The reaction by BmPP is slower than that by kainic acid. The muscular contraction induced by BmPP was not inhibited by L-glutamic acid (FIG. 4). Since the muscular contraction induced by kainic acid is inhibited by L-glutamic acid, these results strongly suggest that the muscular contraction by BmPP is induced through the different pathway from that of kainic acid.

Example 3

Inhibition of Peptideglycan-Induced Muscular Contraction by Anti-BmPP Antibody

The muscular contraction induced by BmPP is inhibited by the anti-BmPP antibody. It was examined whether the muscular contraction induced by peptideglycan was inhibited by the anti-BmPP antibody or not.
<Method>
After injecting 0.05 mL of rabbit antiserum against BmPP into the body cavity of the isolated head muscle specimen of the silkworm larva, immediately 0.05 mL of 0.4 µg/mL of the BmPP solution or the peptideglycan (in this Example, autoclaved *Staphylococcus aureus* was used) suspension was injected, and the body length when the maximum contraction was exhibited (after about 10 minutes) was measured and the C value was calculated in the same manner as in Example 1. As the control experiment, 0.9% NaCl in place of the rabbit antiserum against BmPP was injected.
<Results>
The results are shown in FIG. 5.

Figure 5:
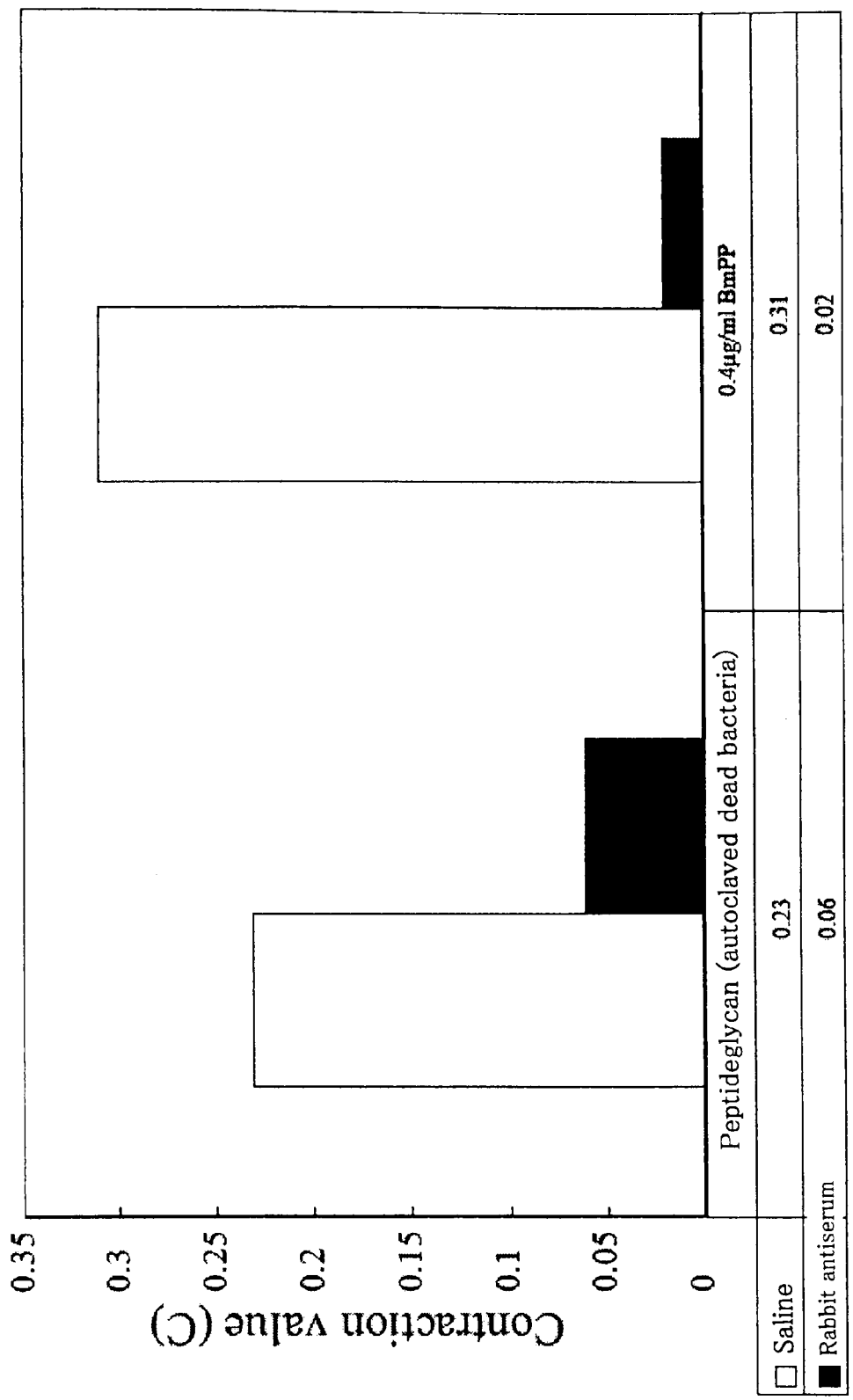
FIG. 5 is a graph showing the effects of an anti-BmPP antibody on the muscular contraction induced by BmPP and peptideglycan in the silkworm larvae.

It was found that the muscular contraction induced by peptideglycan in the silkworm larva was inhibited by the anti-BmPP antibody (FIG. 5). This result suggests that BmPP is required in the muscular contraction induced by peptideglycan. Combined with the result that BmPP itself causes the muscular contraction, it is conceivable that peptideglycan causes the muscular contraction by changing a BmPP precursor present in the body cavity of the silkworm larva to an activated BmPP.

As described above, by having found the mechanism in which peptideglycan known as the innate immunity activation substance causes the muscular contraction, it has been demonstrated that the presence or absence (or its degree) of the innate immunity activation action can be evaluated by evaluating whether the muscle is contracted or not (or its degree).

Example 4

Inhibition of Muscular Contraction by Radical Scavenger

It has been known that BmPP is activated by oxygen in air (e.g., see Kamimura M. et al., Molecular cloning of silkworm paralytic peptide and its developmental regulation. Biochem, Biophys. Res. Commun. 286, 67-73, 2001). It is likely that the activation of BmPP by peptideglycan in the isolated head muscle specimen of the silkworm larva is caused by an active oxygen species induced as a result of an event in which peptideglycan is bound to a receptor protein of peptideglycan present on the immunocompetent cell or the body fluid.

It is likely that the decrease of the active oxygen species inhibits the activation of BmPP to make it difficult to cause the muscular contraction. In order to examine this point, the present inventors examined whether radical scavenger that inhibits the action of active oxygen had an inhibitory effect on the muscular contraction induced by peptideglycan or not.
<Method>
After 0.05 mL of N-acetylcysteine (200 mM) known as the radical scavenger was injected into the body cavity of the isolated head muscle specimen of the silkworm larva, 0.05 mL of air, 0.05 mL of the 0.9% NaCl solution (or suspension)

of peptideglycan (in this Example, autoclaved *Staphylococcus aureus* was used), 125 mM $H_2O_2$, 0.2 mM kainic acid or 0.4 µg/mL BmPP was injected, and the body length when the maximum contraction was exhibited (after about 10 minutes) was measured and the C value was calculated in the same manner as in Example 1.
<Results>

Figure 6:
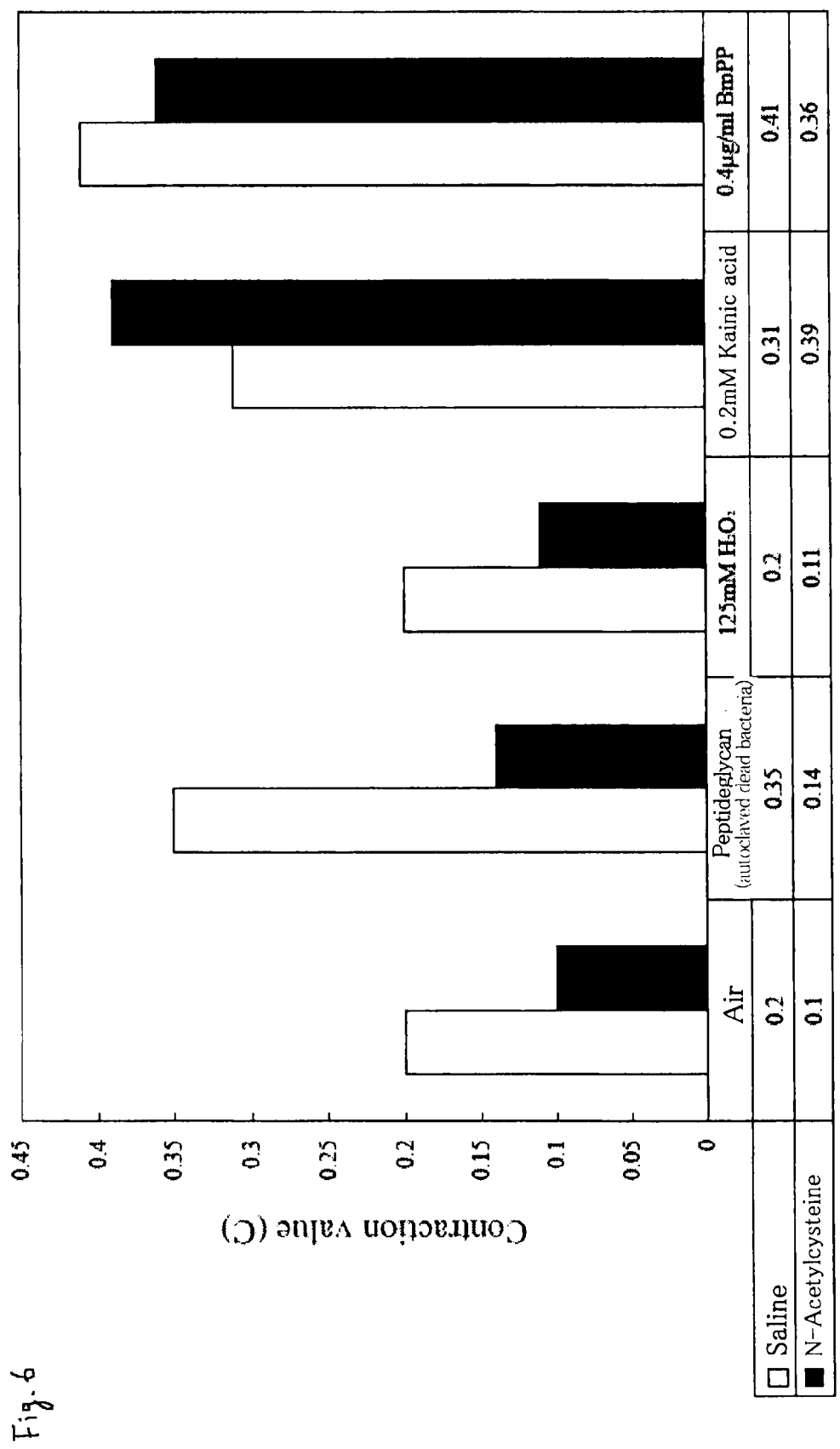
FIG. 6 is a graph showing the effects of N-acetylcysteine on the muscular contraction induced by BmPP and peptideglycan and the like in the silkworm larvae.

The results are shown in FIG. 6.

It was found that N-acetylcysteine known as the radical scavenger inhibited the muscular contraction induced by the air, peptideglycan or $H_2O_2$ (FIG. 6). N-acetylcysteine exhibited no inhibitory effect on the muscular contraction induced by kainic acid or BmPP.

From these results, as described above, the mechanism has been suggested in which peptideglycan is bound to the receptor protein of peptideglycan present in the immunocompetent cell or the body fluid, thereby inducing the active oxygen species and then BmPP is activated by this active oxygen species, resulting in the muscular contraction in the silkworm larva.

Also, this result strongly suggests that the substance that suppresses the innate immune mechanism can be searched using the suppression of the muscular contraction in the silkworm larva as the indicator.

Example 5

Effect of LPS on Muscular Contraction in Silkworm Larva

Lipopolysaccharide (LPS) derived from gram-negative bacteria is known as a promoting substance for the innate immunity (e.g., see Immunology 5th version, Janeway et al., 2001, Garland Publishing). It has been described that the action of LPS is generally observed at 1 µg/mL or less. Concerning LPS derived from various bacteria, the present inventors examined the muscular contraction action in the isolated head muscle specimens of the silkworm larvae.
<Method>

LPS (Sigma) derived from various bacteria was injected into the body cavity in the isolated head muscle specimen of the silkworm larva, the body length was measured after 6 minutes, and the C value was calculated in the same manner as in Example 1. By further injecting 0.2 mL of the air, it was confirmed that the muscular contraction ability of the specimen was not lost.
<Results>

The results are shown in FIG. 7.

LPS (all from Sigma) derived from *Escherichia coli*, *Vibrio cholerae*, *Pseudomonas aeruginosa*, *Klebsiella pneumoniae* and *Shigella flexneri* at 1.3 µg and 12.5 µg (based on 4 g of the silkworm larva) exhibited no muscular contraction action (FIG. 7).

Since the C values of 0.25 to 0.33 were obtained by injecting 0.2 mL of air, it was demonstrated that the muscular contraction ability is present.

It has been reported that when LPS is injected into the silkworm larva, an antibacterial protein is induced in the cell of a fatty body. Therefore, it seems that the innate immune system in the silkworm larva potentially comprises the ability to respond to LPS. However, on the other hand, the presence of a protein that forms a complex by binding to LPS has been reported in the body fluid of the silkworm larva. It is conceivable that no apparent muscular contraction is induced by LPS in the silkworm larva because this protein absorbs LPS.

Example 6

Muscular Contraction and Antiviral Action by Vegetable Extracts

Concerning hot water extracts of the vegetables utilized as the foods, a muscular contraction activity in the silkworm larva was examined, and as a result, it was evaluated whether the vegetable had the action of activating the innate immunity or not. Their action of activating the innate immunity was also confirmed.
<Method>

Each vegetable (carrots, burdocks, cilantro leaves, bell peppers, broccolis, parsleys, pumpkin, Welsh onions (roots), cucumber, rape blossoms, gingers, marsh grass, garlic, Japanese radish, pea shoots, cabbage) was lyophilized and pulverized in a mortar, and then 5 mL of distilled water was added to 1 g of each sample, and centrifuged at 8,000 rpm for 5 minutes. Subsequently, 3 mL of distilled water was added to each pellet, and the treatment with heat at 121° C. for 20 minutes was given to it using an autoclave. This was centrifuged at room temperature at 8,000 rpm for 10 minutes to obtain a supernatant, which was used as a hot water extract. The hot water extract sample was diluted with 0.9% NaCl so that a dilution rate was 0.001 to 1% by mass, 0.05 mL thereof was injected into the body cavity in the isolated head muscle specimen of the silkworm larva, the body length was measured after 6 minutes, and the C value was calculated in the same manner as in Example 1. Here, the "dilution rate" is % by mass of the hot water extract sample based on an entire solution obtained by diluting with the aqueous solution of 0.9% NaCl. Five kinds of the hot water extracts of the vegetables were mixed in equal amounts, and used as a mixture.

After injecting baculovirus into the body fluid in the silkworm larva, 0.05 mL of the hot water extract of the carrot was injected into the body fluid. As the control, the baculovirus alone or 0.9% NaCl alone in place of the baculovirus was injected.
<Results>

Figure 8:
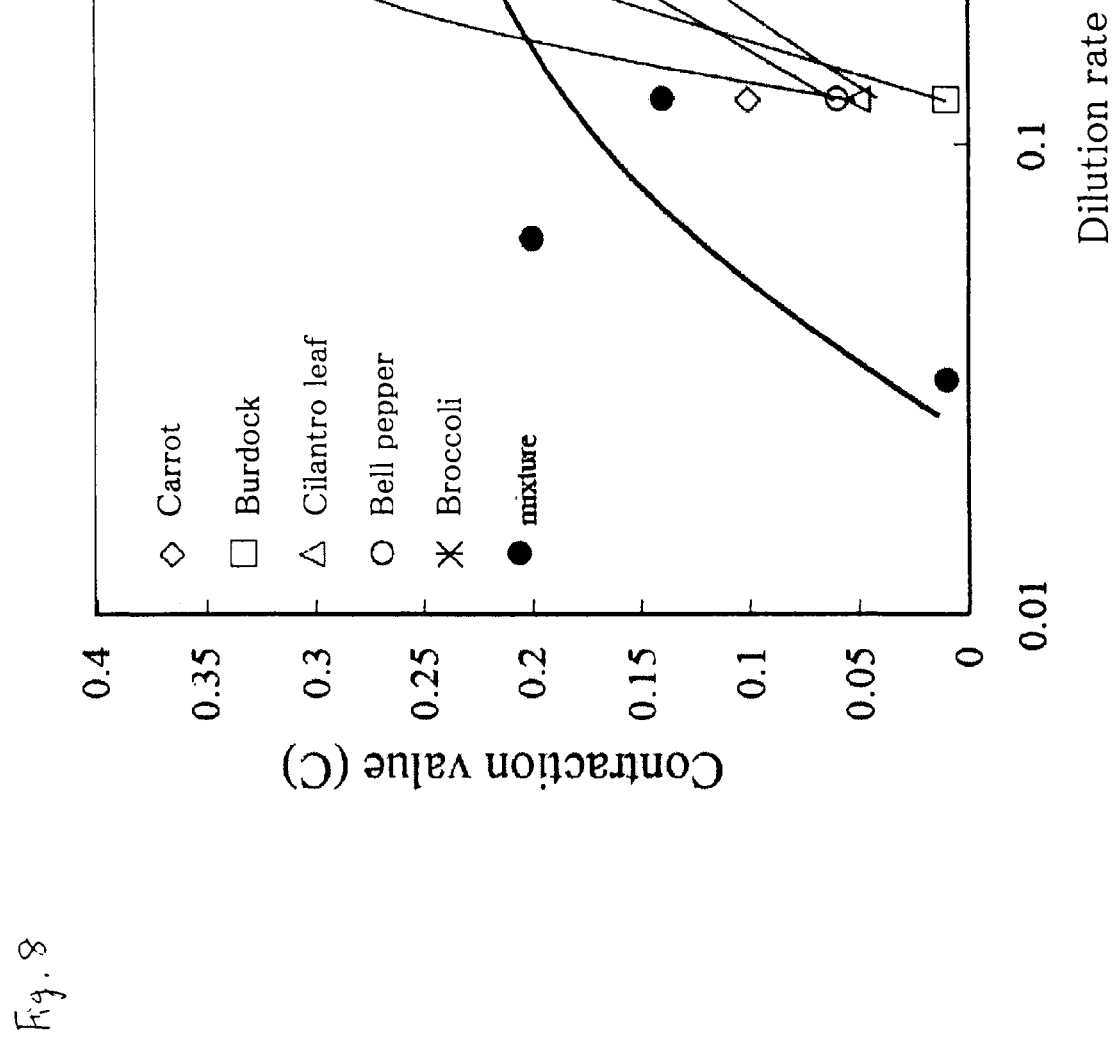
FIG. 8 is a graph showing the muscular contraction caused by extracts from vegetables with hot water in the silkworm larvae.
Figure 9:
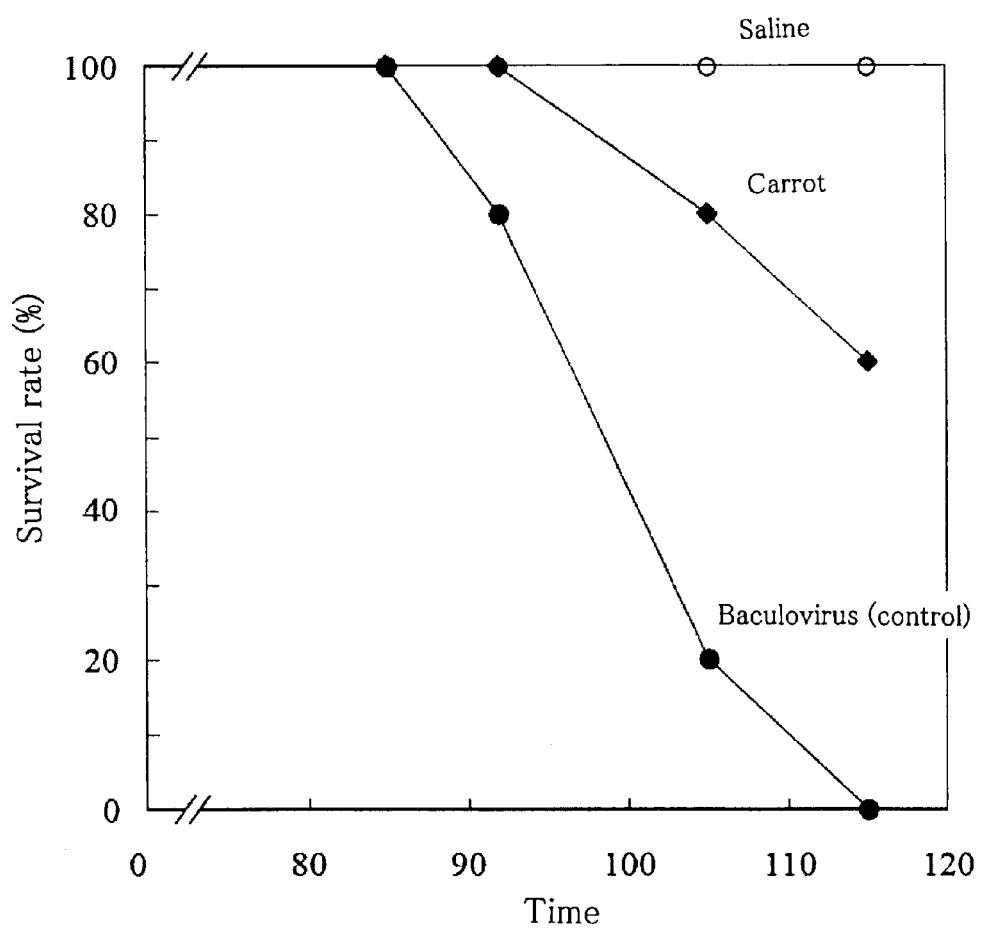
FIG. 9 is a graph showing therapeutic effects of the extracts from the vegetables with hot water on death of silkworm larvae from infection with baculovirus.

The results are shown in FIGS. 8 and 9.

All of the hot water extracts from the carrots, the burdocks, the cilantro leaves, the bell peppers and the broccolis exhibited the muscular contraction activity in the silkworm larvae (FIG. 8). Although the results were not shown in the figure, all of the hot water extracts from the parsleys, the pumpkin, the Welsh onions (roots), the cucumber and the rape blossoms exhibited the muscular contraction activity in the silkworm larvae. Also in the case of mixing the five kinds of the hot water extracts of the vegetables to make the mixture, the muscular contraction activity was not lost and was clearly observed (FIG. 8).

Meanwhile, the gingers, the marsh grass, the garlic, the Japanese radish, the pea shoots and the cabbage at any dilution rate did not cause the muscular contraction in the silkworm larvae (not shown in the figure). Therefore, it is conceivable that the method of screening the innate immunity activation substance using the muscular contraction activity in the silkworm larva as the indicator in the present invention is effective for detecting the innate immunity activation substance contained in the plants such as the vegetables.

Further, the present inventors found that the hot water extract of the carrot that exhibited the muscular contraction activity in the silkworm larva also exhibited the activity to treat viral infection (FIG. 9). In the group infected with the baculovirus alone, all of the silkworm larvae died after 115 hours, but in the group injected with the carrot extract, 60% of the silkworm larvae were alive.

Accordingly, it was suggested that the substance of activating the innate immune system to augment a resistance force against the virus was present in the hot water extract of the carrot. Thus, it was identified that the substance exhibiting the muscular contraction activity in the silkworm larva activated the innate immune system.

Example 7

Purification of Innate Immunity Activation Substance from Turmeric Powder

The turmeric is widely and generally sold as the health food. Among them, in order to obtain the ingredient having the action of activating the innate immune system, the turmeric powder was purified using the muscular contraction in the silkworm larva as the indicator.

<Method>

The turmeric powder (12 g) was suspended in 180 mL of distilled water and autoclaved at 121° C. for 20 minutes. After being centrifuged at room temperature at 8,000 rpm for 25 minutes, a supernatant was collected, a half amount of ethyl alcohol (final concentration 33%) was added, and a resulting precipitate was removed by centrifugation. Further, ethyl alcohol at a final concentration of 67% was added, cooled on ice for 30 minutes, a resulting precipitate was collected by centrifugation, and dissolved in 50 mM Tris-HCl (pH 7.9). This solution was applied on a DEAF cellulose column (40 mL). A substance adsorbed to the column was eluted by a total amount of 200 ml with gradient of 0 to 1 M of NaCl. A volume of each fraction was 1.5 mL. The muscular contraction activity of the silkworm larva in each fraction was examined. Each fraction (0.05 mL) was injected into the body cavity of the isolated head muscle specimen of the silkworm larva, and the body length when the maximum contraction was exhibited (after about 10 minutes) was measured and the C value was calculated in the same manner as in Example 1.

<Results>

Figure 10:
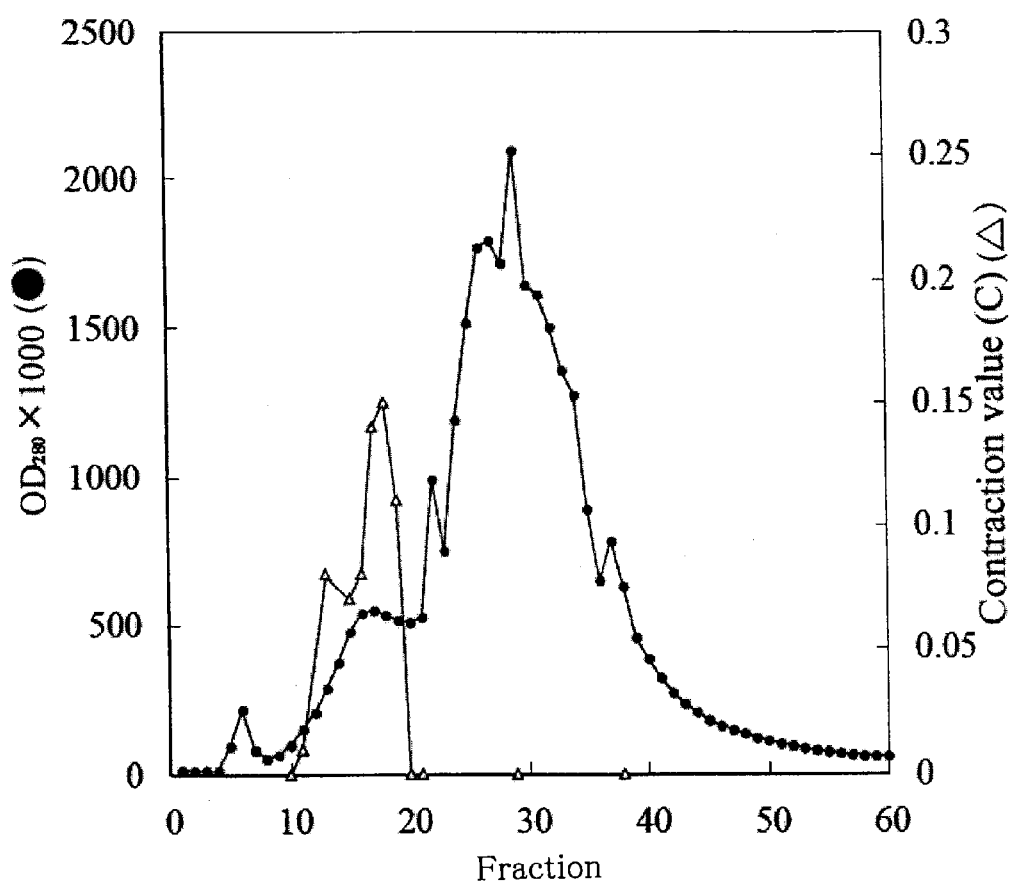
FIG. 10 is a graph showing a result of DEAE cellulose column chromatography of fractions containing a substance that induced muscular contraction of the silkworm larvae in an extract from turmeric with hot water.

The results are shown in FIG. 10.

The present inventors found that the substance that induced the muscular contraction in the isolated head muscle specimen of the silkworm larva was contained in the hot water extract from the turmeric. This active ingredient was recovered in the 33% ethyl alcohol supernatant fraction and the 67% ethyl alcohol precipitate fraction. This fraction was further applied on the DEAE cellulose column chromatography, and the active ingredient was adsorbed to the column and eluted as a single peak by the NaCl gradient (FIG. 10). This result suggests that the active ingredient is a relatively homogenous weak acidic substance.

Example 8

Activation Effect of Substance Purified from Turmeric Powder on Macrophages

It was identified as follows that the "substance purified from the turmeric powder that exhibited the muscular contraction activity in the silkworm larva" activated the innate immune system in the mammalian animal, in Example 7.

<Method>

A suspension (0.1 mL) of murine peritoneal macrophages at $1 \times 10^6$/mL was dispensed in each well in a 96-well plate, the hot water extract of the turmeric or the DEAE cellulose-purified fraction of the turmeric was added, the plate was incubated for two days, and subsequently the amount of IL-6 in the culture supernatant was quantified by ELISA method.

<Results>

Figure 11:
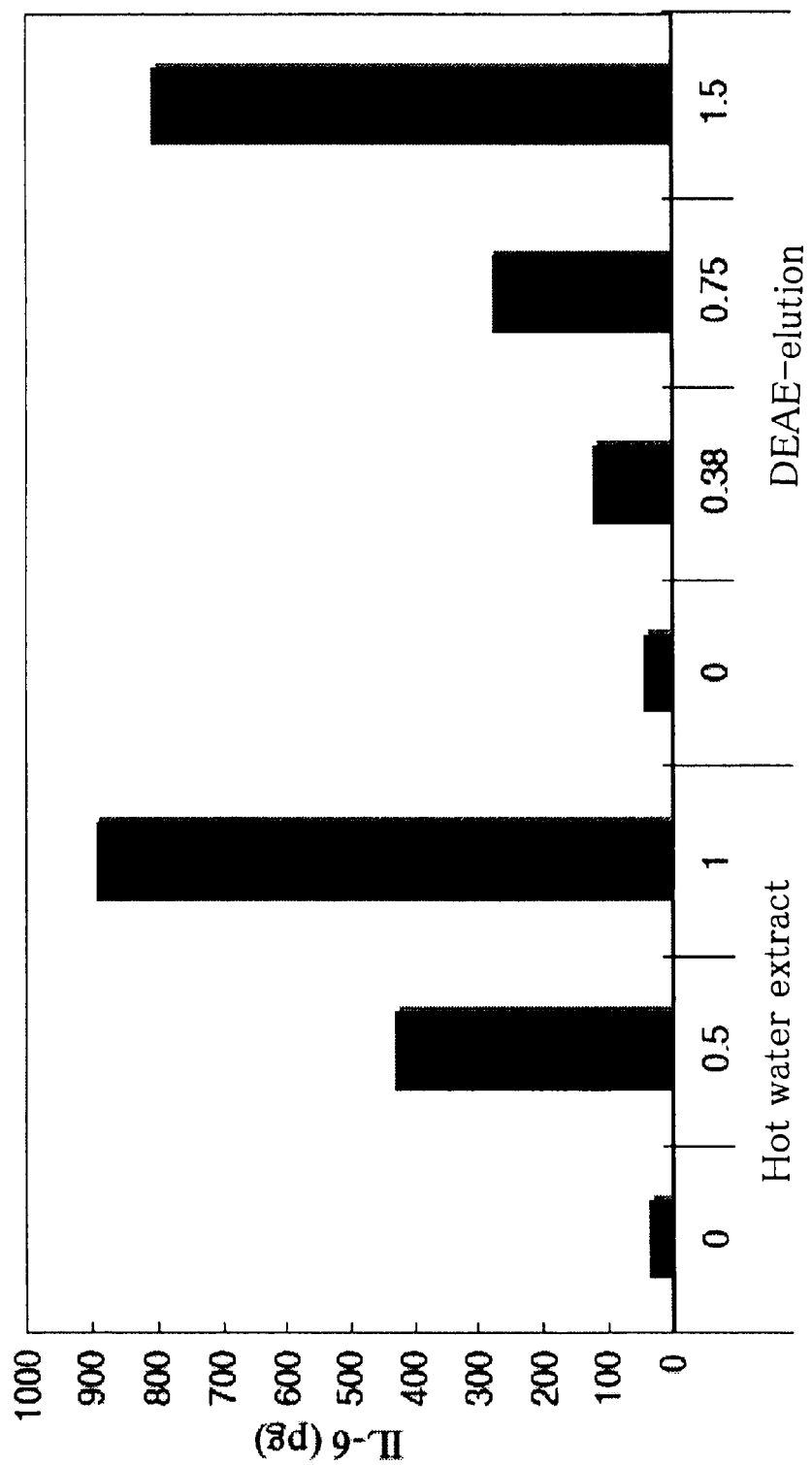
FIG. 11 is a graph showing activation of murine macrophages by the extract from the turmeric powder with hot water and by its fraction purified by DEAE cellulose column chromatography.

The results are shown in FIG. 11. A numeral on a horizontal axis in FIG. 11 shows an active unit in each isolated head specimen of the silkworm larva when the muscular contraction activity when the C value is 0.15 is defined as one unit. That is, numerals on the horizontal axis show the innate immunity activation activity using the muscular contraction in the silkworm larva as the indicator. The activity to cause the contraction of 15% muscle is one unit. The hot water extract and the DEAE eluted fraction were diluted with saline serially two times, and then added to the reaction system.

The activity of the hot water extract of the turmeric and the purified fraction by the DEAE cellulose column chromatography of the turmeric powder were examined for the murine peritoneal macrophages, and it was found that both of them promoted the release of IL-6. The intensity of this IL-6 releasing activity was correlated to the intensity of the muscular contraction activity in the silkworm larvae (FIG. 11). Therefore, both activities appear to be derived from the identical substance.

This result strongly suggests that the innate immunity activation substance in the mammalian animals can be evaluated and screened (searched) using the muscular contraction in the silkworm larva as the indicator. It has been already known that the insects and the mammalian animals have the common mechanism in the innate immune system, and this fact also claims a rationality of the above result on the present invention.

Effects/Uses

From the results of respective Examples described above, the present inventors reached a new concept that the activation of a muscular contraction system is associated with the activation of the innate immune system in the silkworm larva, i.e., the both systems are coupled, the concept not being conventionally present at all.

It has been already known that the peptide BmPP present in the body fluid in the silkworm larva causes the paralysis of the silkworm larva, but the present inventors further demonstrated for the first time that BmPP contracted the muscle in the silkworm larva (Example 2).

Further, the present inventors have demonstrated that peptideglycan known for activating the innate immune mechanism causes the muscular contraction (Example 1) and that the antibody against BmPP inhibits this muscular contraction (Example 3). Therefore, it was revealed that peptideglycan contracted the muscle through BmPP.

The muscular contraction via peptideglycan was inhibited by the radical scavenger (Example 4). A rationale description for these results is that the activation of BmPP is caused by the increase of the active oxygen species amount in the blood in conjunction of the activation of the innate immune system by peptideglycan, thereby inducing the muscular contraction. That is, the innate immune system is coupled with the muscular contraction system. And by having demonstrated an inevitable correlation between the innate immune system and the muscular contraction system, it was elucidated that the activation of the innate immune system could be evaluated by evaluating the muscular contraction activity.

Figure 12:
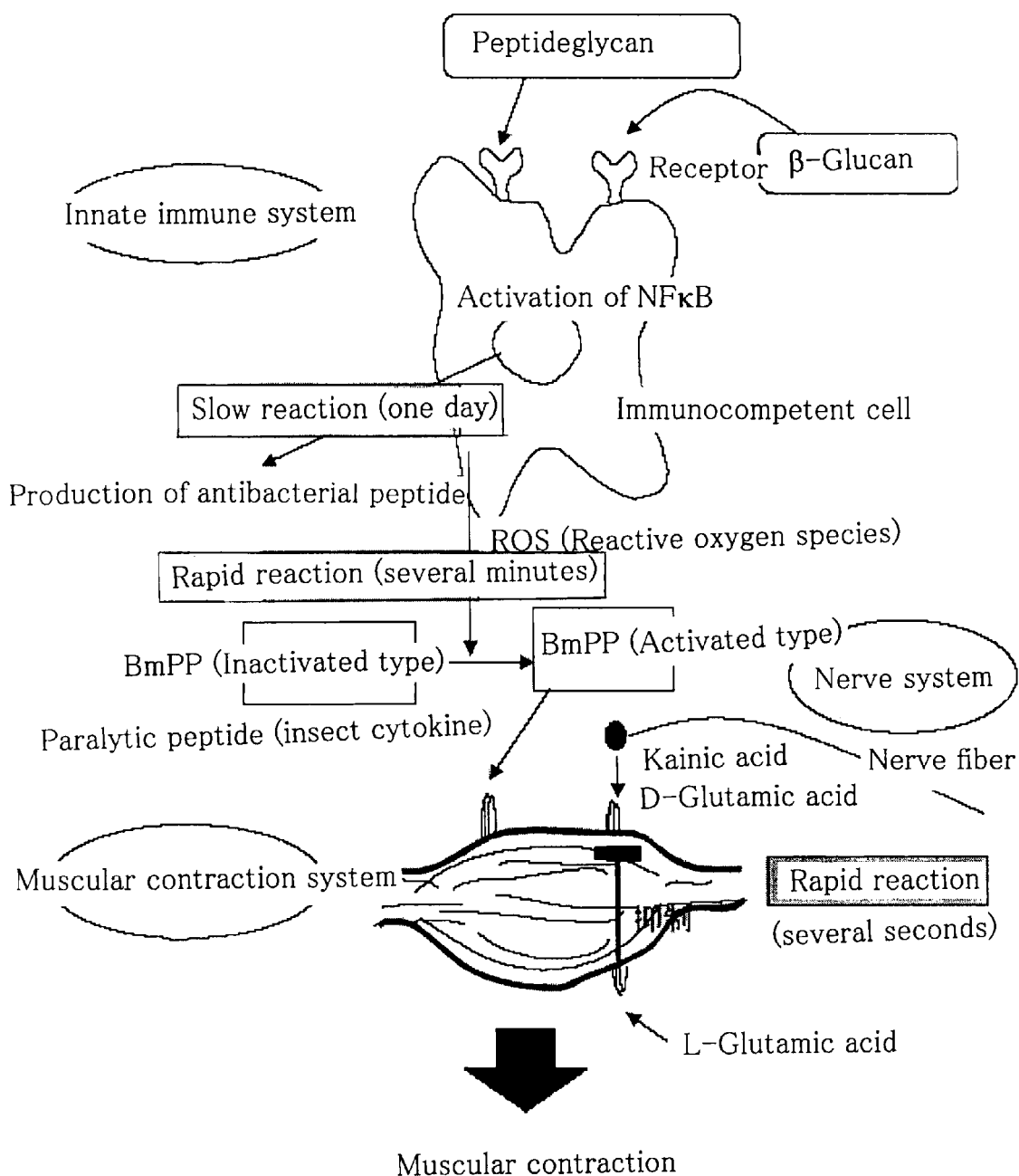
FIG. 12 is a view showing an association between an innate immune system and a muscular contraction system in the silkworm larva, suggested from the results in Examples 1 to 8.

The association between the innate immune system and the muscular contraction system suggested from the results in the aforementioned Examples are shown in FIG. 12. Peptideglycan and β-glucan are bound to the receptors on the immunocompetent cells (or humoral) and result in the production of the active oxygen species (ROS). This promotes the cascade of proteases to lead to the change the paralytic peptide BmPP in the silkworm larva from the precursor (inactivated type) to the activated type. Activated BmPP directly (or indirectly) acts upon muscular cells to promote the muscular contraction. This pathway is different from the muscular contraction pathway by kainic acid through the stimulation of the nerve in that this pathway takes several minutes and L-glutamic acid can not inhibit this pathway (Examples 1 and 2).

Based on this idea, it is possible to screen (search) a novel innate immunity activation substance using the muscular contraction of the organism such as the silkworm larva having the innate immune mechanism as the indicator. Actually, in the present invention, the Examples using the vegetables such as carrot and turmeric were shown, and it was shown that the ingredient contained in these vegetables had the therapeutic effect on the infection of the silkworm larvae with the baculovirus as well as activated the murine macrophages (Examples 6 to 8). It is anticipated that it is possible to discover the novel innate immunity activation substances from various natural products utilizing the present invention to make them work for the prevention or the treatment of various diseases in the human beings.

Conventionally, when the innate immunity activation substance is searched, the method in which the material to be tested is added to the cultured immunocompetent cells such as macrophages and the release of the cytokine such as IL-6 or TNF-α is detected by ELISA has been employed. However, in such a conventional method, the equipments for culturing the cells are required, and there has been the problem that the substance that potentially disturbs the in vivo kinetics in the individual when administered to the individual is also detected. Also, lipopolysaccharide (LPS) derived from bacteria, which is contaminated in a small amount in the material to be tested reacts to make many materials to be tested false positive, and this has been the obstacle in the search of the novel substance.

On the contrary, in the screening method of the present invention using the muscular contraction of the silkworm larva as the indicator, the equipment for culturing the cells is unnecessary, and it becomes possible to search the innate immunity activation substance extremely simply and easily. Since the material to be tested is administered to the individual such as the silkworm larva, the substance that potentially disturbs the in vivo kinetics can be excluded. Since LPS derived form the bacteria at the concentrations used in Example did not cause the muscular contraction in the silkworm larva (Example 5), it is possible to solve the problem of the false positive due to LPS derived from the bacteria and contaminated in the material to be tested.

According to the present invention, in addition that it becomes possible to search the novel innate immunity activation substance, it also becomes possible to purify the compound exhibiting a medicinal effect from the natural products such as known natural foods and Chinese herbal medicines, whose mechanism for its potency is not elucidated yet.

In the present invention, it is conceivable that the search of the novel innate immunity activation substance can be carried out more efficiently by combining the conventional search method of the innate immunity activation substance using the cultured cells. The innate immunity activation substance evaluated and searched according to the present invention is suitable for various intended uses, e.g., the health maintenance, the recovery from the fatigue, and the prevention or the treatment of the cancer.

The present invention is suitably used for evaluating and searching not only the innate immunity activation substance but also the innate immunity suppression substance. The innate immunity suppression substance evaluated and searched according to the present invention is suitable for various intended uses, for example as an immunosuppressant and an anti-inflammatory agent.

INDUSTRIAL APPLICABILITY

The evaluation method and the screening method, as well as the drug, the food and the method of producing the same of the present invention are very useful for evaluating and screening the substance having the action of activating/suppressing the innate immune mechanism, and are very useful for developing the innate immunity activator/the food having innate immunity activation action and the innate immunity suppressor/the food having innate immunity suppression action.

The present application is based on JP 2007-102918 that is Japanese Patent Application filed on Apr. 10, 2007, all contents of this application are cited here and incorporated herein as disclosure of the specification of the present invention.

The invention claimed is:

1. A method of evaluating an innate immune mechanism activity of a test material, the method comprising
   (a) administering said test material to an isolated head muscle sample of a silkworm larva; and
   (b) evaluating whether said test material contracts a muscle of the isolated head muscle sample of a silkworm larva, wherein the muscle contraction indicates that the test material has innate immune mechanism activity.

2. A method of screening for a test material that activates an innate immune mechanism, the method comprising
   (a) administering the test material to an isolated head muscle sample of a silkworm larva;
   (b) evaluating whether said test material contracts the isolated head muscle of a silkworm larva, wherein the muscle contraction indicates that the test material activates the innate immune mechanism; and
   (c) selecting the test material that contracts the isolated head muscle sample of a silkworm larva.

3. A method of evaluating whether a test material suppresses an innate immune mechanism or not, the method comprising
   (a') administering said test material and an innate immunity activation material to an isolated head muscle sample of a silkworm larva; and
   (b') evaluating whether said test material suppresses contraction of the isolated head muscle sample of the silkworm larva in the presence of the innate immunity activation material, wherein the suppression of muscle contraction indicates that the test material has innate immune suppression activity.

4. The method of claim 3, wherein the innate immunity activation material is peptideglycan, β-glucan, killed bacteria, or fungi.

5. A method of screening for a test material that suppresses an innate immune mechanism, the method comprising
(a') administering the test material and an innate immunity activation material to an isolated head muscle sample of a silkworm larva;
(b) evaluating whether said test material suppresses contraction of the isolated head muscle sample of a silkworm larva in the presence of the innate immunity activation material; and
(c') selecting the test material that suppresses the contraction of the muscle of the isolated head muscle sample of a silkworm larva, wherein the suppression of muscle contraction indicates that the test material has innate immune suppression activity.

6. The method of claim 5, wherein the innate immunity activation material is peptideglycan, β-glucan, killed bacteria, or fungi.